(12) United States Patent
Madhavan et al.

(10) Patent No.: US 10,586,020 B2
(45) Date of Patent: Mar. 10, 2020

(54) TELEMEDICINE COMPONENTS, DEVICES, APPLICATIONS AND USES THEREOF

(71) Applicant: Tiatech USA, Inc., Southfield, MI (US)

(72) Inventors: Ramesh Madhavan, Troy, MI (US); Jitin Ranjit, Thrissur (IN)

(73) Assignee: Tiatech USA, Inc., Southfield, MI (US)

( * ) Notice: Subject to any disclaimer, the term of this patent is extended or adjusted under 35 U.S.C. 154(b) by 1356 days.

(21) Appl. No.: 14/695,966

(22) Filed: Apr. 24, 2015

(65) Prior Publication Data

US 2015/0310183 A1    Oct. 29, 2015

Related U.S. Application Data

(60) Provisional application No. 61/984,443, filed on Apr. 25, 2014.

(51) Int. Cl.
*G06Q 50/00* (2012.01)
*G06F 19/00* (2018.01)
*G16H 10/60* (2018.01)

(52) U.S. Cl.
CPC ......... *G06F 19/3418* (2013.01); *G16H 10/60* (2018.01)

(58) Field of Classification Search
None
See application file for complete search history.

(56) References Cited

U.S. PATENT DOCUMENTS

| 4,469,107 | A | 9/1984 | Asmar et al. |
| 5,652,630 | A | 7/1997 | Bertram et al. |
| 7,185,282 | B1* | 2/2007 | Naidoo ............... A61B 5/0002 348/E7.071 |
| 9,043,217 | B2 | 5/2015 | Cashman et al. |
| 2005/0007878 | A1 | 1/2005 | Chen |
| 2008/0013747 | A1 | 1/2008 | Tran |
| 2008/0129518 | A1* | 6/2008 | Carlton-Foss ........ A61B 5/1117 340/573.1 |
| 2009/0240125 | A1 | 9/2009 | Such et al. |
| 2011/0009707 | A1 | 1/2011 | Kaundinya et al. |
| 2011/0088964 | A1* | 4/2011 | MacMackin ............. A61B 7/02 181/131 |
| 2011/0119028 | A1 | 5/2011 | Bishop |
| 2011/0234409 | A1 | 9/2011 | Soliman |
| 2012/0179479 | A1 | 7/2012 | Waterson et al. |
| 2012/0234409 | A1 | 7/2012 | Waterson et al. |
| 2014/0073880 | A1 | 3/2014 | Boucher et al. |

OTHER PUBLICATIONS

International Search Report and Written Opinion of the International Searching Authority dated Sep. 23, 2015, which issued during prosecution of International Application No. PCT/US15/27594.

* cited by examiner

*Primary Examiner* — Jonathan Ng
(74) *Attorney, Agent, or Firm* — Dierker & Kavanaugh, P.C.

(57) ABSTRACT

The present invention relates to equipment including hardware, software, and methods of use thereof for enabling medical interactions between individuals in separate locations. More specifically, the present invention relates to telemedicine components, devices, applications, and uses thereof. Embodiments of the present invention enable video, audio, textual, and graphical information to be securely exchanged between doctors and patients, as well as data files. A doctor located remotely from a patient may receive information from and control one or more medical devices located proximate to the patient using software operating on a computing device.

12 Claims, 14 Drawing Sheets

TELEMEDICINE COMPONENTS, DEVICES, APPLICATIONS AND USES THEREOF

CROSS REFERENCE TO RELATED APPLICATIONS

This application claims the benefit of U.S. Provisional Patent Application Ser. No. 61/984,443, filed Apr. 25, 2014 for "Telemedicine Components, Devices, Applications And Uses Thereof" by Ramesh Madhavan and Jitin Ranjit, the disclosure of which is incorporated herein by reference in its entirety.

FIELD OF THE INVENTION

The present invention relates to equipment including hardware, software, and methods of use thereof for enabling interactions between individuals in separate locations. More specifically, the present invention relates to telemedicine components, devices, applications, and uses thereof.

BACKGROUND

Telemedicine involves the use of telecommunication and information technologies to provide clinical health care from a distance. Telemedicine enables a physician to provide clinical advice, such as a diagnosis, to a patient in another geographical location. Previously, telemedicine was performed using telephones, fax machines, or radios. For example, one physician might communicate a patient's symptoms to another using a radio, so as to obtain advice on the best course of treatment. Similarly, a patient in South Africa might fax his or her medical records to a physician located in the United States. The physician could then make a telephone call to the patient in order to give the patient an opinion regarding the patient's affliction.

However, these basic forms of telemedicine suffered from significant disadvantages. Diagnosis and treatment were more difficult and time-consuming than if a physician were in the same location as his or her patient, as remotely located physicians were unable to directly perform tests upon their patients. Poor-quality transmission of records, such as blurred black and white photographs, could lead to the misdiagnosis of patients. Therefore, a long-standing and unaddressed need exists for improved telemedicine components, devices, and applications to allow physicians to efficiently and effectively provide medical treatment to patients in geographically remote locations.

Citation or identification of any document in this application is not an admission that such document is available as prior art to the present invention.

SUMMARY

Embodiments of the present invention utilize developments in advanced telecommunication and information technologies, including video-telephony and robotics, to enable significant improvements to telemedicine.

In accordance with an embodiment of the present invention, a physician and patient may interact using videoconferencing and/or teleconferencing over an encrypted communication channel and may simultaneously exchange data, such as electronic medical records (EMRs). A physician may use software such as an application on a computer or portable computing device to remotely access medical data such as EMRs and test results, remotely administer tests, and communicate directly with a patient in a separate location.

In accordance with an embodiment, a physician may use software on a computer or portable computing device to control medical equipment such as a microscope located proximate to a patient. The physician may receive the results of medical tests using the software.

In accordance with an embodiment, room automation may be controlled remotely. A physician may adjust the lighting and control other environmental factors in a patient's room.

In accordance with an embodiment, an patient monitoring and alarm system may alert a physician to patient movement or a change in a patient's vital signs.

In accordance with an embodiment, a patient may interact with an animated avatar in order to collect information from the patient, such as a patient history and a listing of the patient's symptoms. This interaction may be recorded using video and/or sound recording. Data, such as the position of the patient's body, may be collected using sensors such as ultrasonic or infrared sensors. This information may be sent to a physician in a separate location and accessed using software running on a computer or portable computing device.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises," "comprised," "comprising" and the like can have the meaning attributed to them in U.S. Patent law; e.g., they can mean "includes," "included," "including," and the like; and that terms such as "consisting essentially of" and "consists essentially of" have the meaning ascribed to them in U.S. Patent law, e.g., they allow for elements not explicitly recited, but exclude elements that are found in the prior art or that effect a basic or novel characteristic of the invention.

These and other embodiments are disclosed or are obvious from and encompassed by the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1:
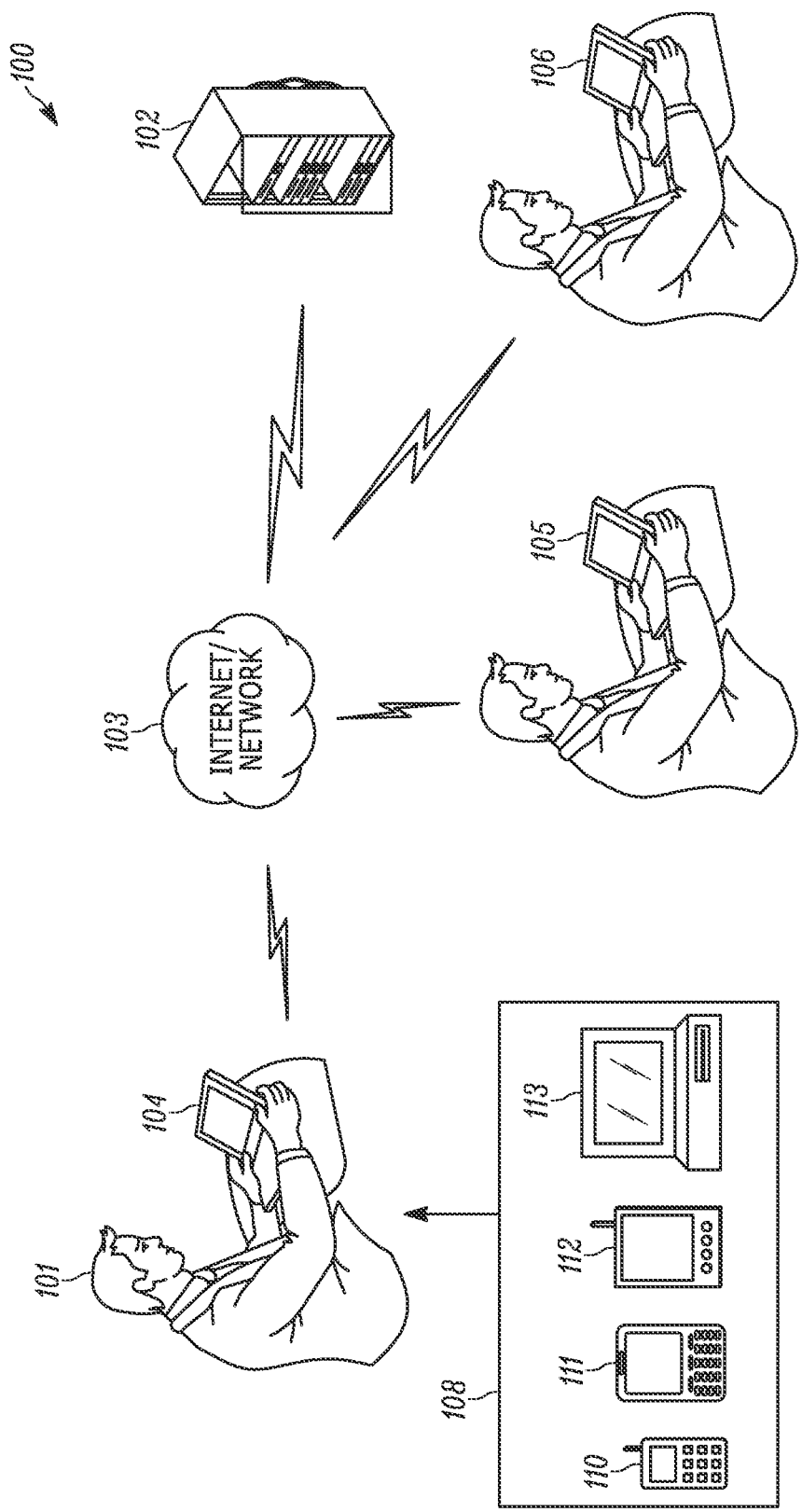
FIG. 1 illustrates a hardware configuration wherein a system in accordance with an embodiment of the present invention may be implemented.

For the purposes of promoting and understanding the principles disclosed herein, reference is now made to the preferred embodiments illustrated in the drawings, and specific language is used to describe the same. It is nevertheless understood that no limitation of the scope of the invention is hereby intended. Such alterations and further modifications in the illustrated devices and such further applications of the principles disclosed and illustrated herein are contemplated as would normally occur to one skilled in the art to which this disclosure relates.

Described herein are embodiments systems comprised of telemedicine components, devices, applications, and uses thereof for enabling patients and physicians in physically separate locations to interact. These systems may be implemented using a variety of hardware running specialized software so as to enable these interactions. Software operates as a set of instructions running in executable memory of a processor residing on a computing device. To fully enable the software and its functionality described herein, the present disclosure begins with a summary of how computing devices may be used, either alone or in a networked configuration.

Overview of Networked Hardware

FIG. 1 illustrates a hardware configuration 100 wherein a system can be implemented on one or more computing devices 104, 105, and 106 used by different users 101 and connected over a network 103. The computing devices may comprise computers 104, 105, and/or base stations 106. The network 103 is suitable for connecting the one or more computers 104, 105, and 106 and may comprise one or more networks such as a local area network (LAN), a wide area network (WAN) such as the Internet, telephone networks including telephone networks with dedicated communication links and/or wireless links, and wireless networks. In the illustrative example shown in FIG. 1, the network 103 is the Internet. Each of the one or more computing devices 104, 105, and 106 is connected to the network 103 via a suitable communication link, such as a dedicated communication line or a wireless communication link. The system may be implemented using software that is either local or operating from a remote server 102 such as a web server over the Internet. Further, with the rapid growth of Internet technology and portable wireless technology, other computing devices, such as but not limited to cell phones 110, handheld devices 111, portable tablets 112, or portable computers 113 may be used place of or in addition to the one or more computing devices 104, 105, and 106.

Each of the one or more computing devices 104, 105, and 106 comprises a central processing unit (CPU) and an input/output (I/O) unit; additionally, the computing devices 104, 105, and 106 may further comprise a display device communicatively coupled to the I/O unit, a storage device, and a memory. In an embodiment, each of the one or more computing devices 104, 105, and 106 further comprises one or more standard input devices such as a keyboard, a mouse, speech processing means, and/or a touchscreen. In an embodiment, the memory includes a Graphical User Interface (GUI) that is used to convey information to and receive information from a user of the one or more computing devices 104, 105, and 106 via the display device and I/O unit as described herein. In an embodiment, the GUI includes any user interface capable of being displayed on a display device including, but not limited to, a web page, a display panel in an executable program, or any other interface capable of being displayed on the one or more computing devices' 104, 105, and 106 respective display device.

As will be recognized by one of skill in the art, each of the cell phones 110, handheld devices 111, different portable tablets 112, or computers 113 may be configured similarly to the one or more computing devices 104, 105, and 106, taking into account the various design considerations of these respective devices.

The GUI may be transmitted to the one or more computing devices 104, 105, and 106 or other devices 110, 111, 112, or 113 via the network 103. In one embodiment in accordance with the present invention, the GUI is displayed using commercially available hypertext markup language ("HTML") viewing software such as, but not limited to, Microsoft Internet Explorer, Google Chrome, Apple Safari, or Mozilla Firefox, or any other commercially available HTML viewing software.

In another embodiment in accordance with the present invention, the GUI is displayed using executable code stored locally on one of the one or more computing devices 104, 105, and 106 or other devices 110, 111, 112, or 113. For example, the GUI may be displayed using a stand-alone executable application or App. The GUI may be updated or modified using information received via the network 103. For example, the stand-alone executable application on one of the computing devices 104, 105, or 106 could display a list of names, where the names are updated using information received via the network 103.

The GUI may reside on a remote server 102. Alternatively, a portion of the GUI or of the information displayed by the GUI may reside on a remote server 102. The remote server 102 may comprise one or more separate servers. The remote server 102 may be a web server. The remote server 102 may comprise a CPU, memory, and separate storage device and be communicatively coupled to the network 103. The remote server 102 may contain an information storage device that may be a rational database, such as Microsoft's SQL or any other database.

Overview of Design

Figure 2:
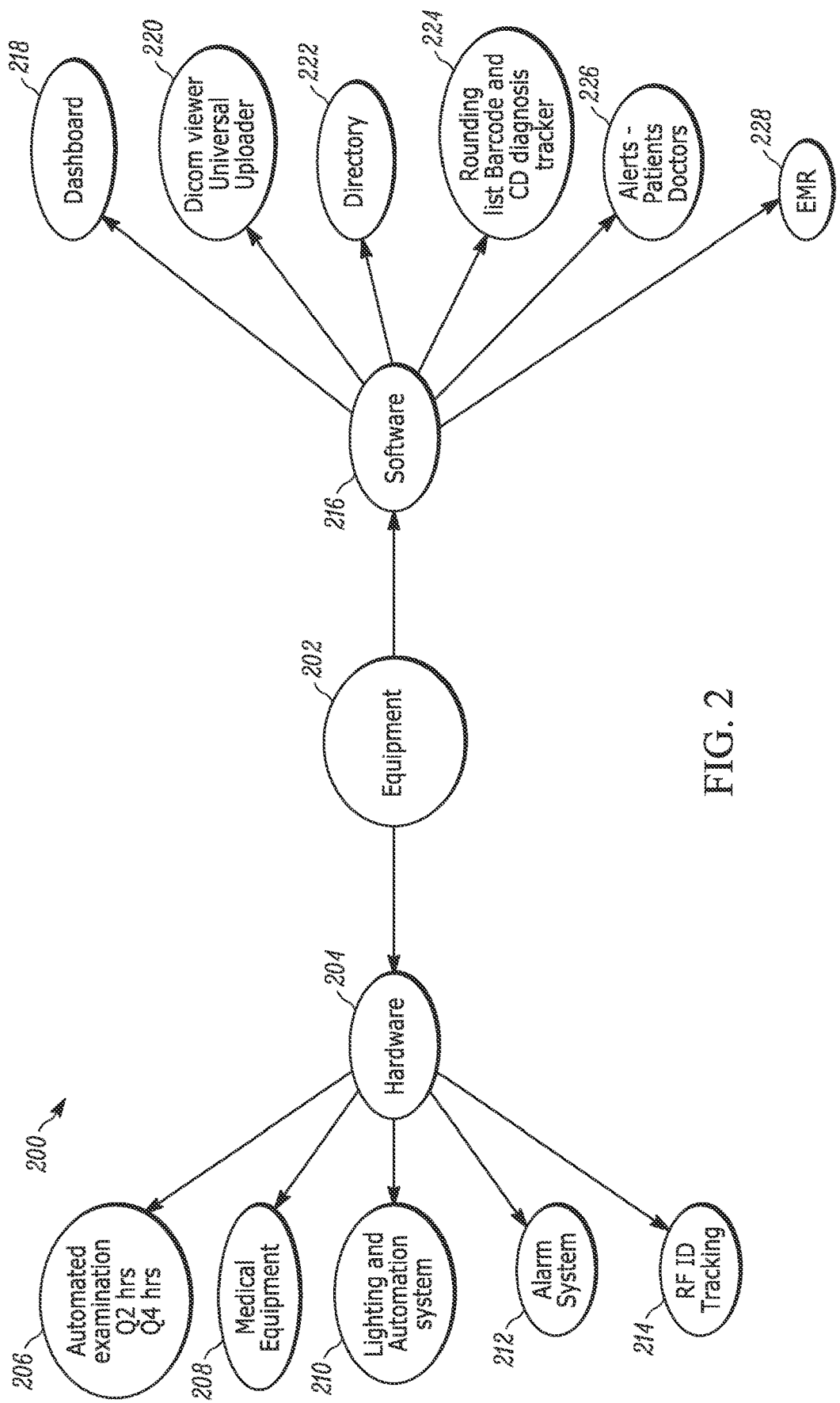
FIG. 2 depicts a block diagram illustrating an overview of a system in accordance with an embodiment of the present invention.

With reference to FIG. 2, a block diagram providing an overview of a system 200 in accordance with an embodiment of the present invention is shown.

Prior to the development of telemedicine, a doctor needed to be physically located near his or her patient in order to formulate a diagnosis and provide treatment. For example, a doctor might need to conduct a basic physical examination of the patient, including measuring her height, weight, and blood pressure. The doctor would likely conduct an interview with the patient, asking her about her symptoms and any relevant family history of illness. Further, he may need to perform tests, such as examining a sample of the patient's blood using a microscope or performing an imaging test using x-rays or magnetic resonance imaging (MRI). Finally, the doctor may need to provide treatment to the patient, for example, by writing a prescription and instructing her as to her treatment regimen. Each of these tasks required that the doctor physically be in the same location as the patient.

In an embodiment, using the system shown in FIG. 2, a doctor performs all of the foregoing tasks without being in the same physical location as the patient. Specialized equipment allows interactions between two individuals, such as a patient and her doctor, who may be in different physical locations. In an embodiment, the equipment 202 includes a server 102 connected to one or more computing devices, such as one or more computers 104, 105, and 106 or other devices 110, 111, 112, or 113, via a network 103.

In an embodiment, the equipment 202 comprises a server 102 connected to at least two computing devices using the Internet. A first computing device (e.g., computer 104) is located in physical proximity to a first person, such as a doctor. A second computing device (e.g., cell phone 110) is located in physical proximity to a second person, such as a patient. These computing devices exchange information between one another using the network 103. The computing devices 104 and 110 may either exchange information directly or indirectly, for example by using the server 102 as an intermediary. By using the computing devices 104, 110, the patient and doctor may interact together, for example by exchanging video, audio, and/or other data. The information may be securely transmitted using encryption. In an embodiment, the information transmitted between the computing devices may be supplemented by additional information sent by the server 102. For example, video data sent by the second computing device 110 may be sent to the first computing device 104; at the same time, additional data (such as an electronic medical history or test results) may be transmitted from the server 102 to the first computing device 104. Alternatively, in an embodiment, a server 102 is not used and the two computing devices 104 and 110 are directly linked via the network 103.

In an embodiment, the system comprises hardware 204 located proximate to a patient. In an embodiment, the hardware 204 comprises a base station 106 that is connected to a WAN such as the Internet. This connection may be either wired or wireless. Using the WAN, the base station 106 communicates with a server 102 or other computing device, such as a computing device 104 located proximate to the doctor. The base station 106 is configured to transmit and receive information (e.g., audio, video, and/or other data) and commands. In an embodiment, the base station is further connected to a LAN, either wirelessly using a communication protocol such as ZigBee (a specification based on the IEEE 802.15 standard), Bluetooth (formerly the IEEE 802.15.1 standard), or Wi-Fi (the IEEE 802.11 standard) or via a wired connection using a communications protocol such as Ethernet or RS-232. In an embodiment, the base station 106 includes input devices, such as a video camera, microphone, and/or keyboard. In an embodiment, the base station 106 includes output devices, such as a display screen and/or speaker. In an embodiment, these input and output devices are used to simulate having the physician physically present in the room with the patient. For example, the display screen may display the physician's face while the speaker emits the physician's voice. The video camera and microphone may record the patient and transmit that information directly to the physician or to the server 102, where the information may be stored or processed. In an embodiment, the physician is similarly recorded by a video camera and/or microphone; this information is transmitted to the base station where it is presented to the patient. Alternatively, in an embodiment, a program running on the server 102 or base station generates visual and/or auditory information that is presented to the patient. In an embodiment, this information is a virtual representation of a physician, including a computer-generated image of a physician's face and computer-generated audio of a physician's voice. Alternatively, this information may be prerecorded video and/or audio of a physician or textual information, such as instructions for the patient.

The hardware 204 may be connected to various devices located proximate to the patient using the LAN. These devices may, for example, include a device configured to perform an automated examination of the patient (e.g., using a video camera and/or microphone) and may include various medical equipment 208 such as a microscope, an environmental control element 210 (also referred to as a lighting and automation system) that may adjust lighting and other automation systems, an alarm system 212, and an RFID tracking system 214. Each of these elements are discussed in greater detail herein. These devices may be controlled by signals sent over the LAN by the base station. Further, these devices may be controlled via signals received by the base station over the WAN and retransmitted to the devices over the LAN. These devices may transmit information, such as the current conditions of the device or measurements obtained regarding the patient, to the base station over the LAN. This information may be retransmitted to another computing device such as the server 102 or the computing device located proximate to the doctor using the WAN.

As discussed above, in an embodiment, the system 200 includes one or more devices to enable a patient and a physician to interact, which may include one or more video cameras, displays, microphones, and speakers. In an embodiment, a device located proximate to the patient includes a video camera, display, microphone, and speaker. A corresponding device located proximate to a physician similarly includes a video camera, display, microphone, and speaker. In an embodiment, the devices are communicatively coupled, enabling videoconferencing between the patient and physician. In an embodiment, one or more of the devices may be a smartphone, tablet, or computer. In an embodiment, the device proximate to the patient is integrated with the base station.

In an embodiment, the system 200 includes a device 206 that performs an automated examination of the patient, for example, by using a display, video camera, and microphone. In an embodiment, a video of a physician asking the patient questions is shown on the display using the device 206 located proximate to the patient. In an embodiment, the video is prerecorded. In an embodiment, the video is artificially generated (e.g., is an animation). The patient's answers are then recorded using the video camera contained in the device 206 located proximate to the patient. In an embodiment, the video or animation instructs the patient to perform certain actions, such as raising the patient's arms above his or her head or using medical equipment 208 (e.g., the patient may be instructed to step onto a scale). The results of these actions are then recorded. In an embodiment, the recorded information is sent to a physician in a separate physical location. In an embodiment, the recorded information is sent to the physician in real time. In an embodiment, the recorded information is saved and shown to the physician at a later time.

In an embodiment, the system comprises software 216. In an embodiment, the software includes a GUI. In an embodiment, the GUI allows a remotely located user to control and interact with the hardware located proximate to a patient, including the base station and various other devices located proximate to the patient. In an embodiment, the software comprises elements including a dashboard 218, a DICOM viewer and universal uploader 220, a directory 222, a diagnosis tracker 224, alerts provided to patients or doctors 226, and electronic medical records ("EMR") 228. Each of these elements is discussed in greater detail herein.

Medical Equipment

Figure 3:
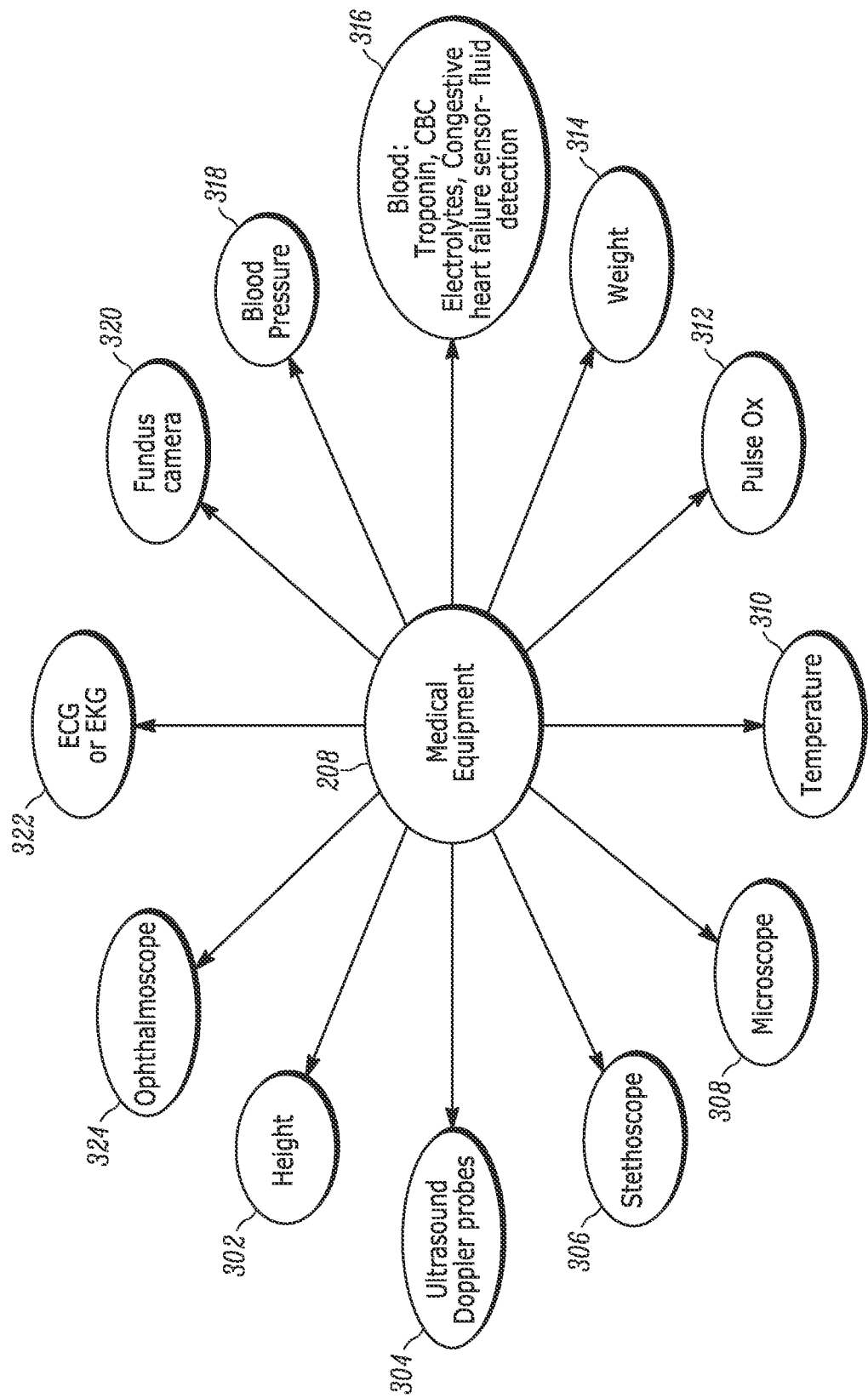
FIG. 3 depicts examples of the medical equipment that may be incorporated into a system in accordance with an embodiment of the present invention.

With reference to FIG. 3, a block diagram depicting an overview of medical equipment 208 in accordance with an embodiment of the present invention is provided. The medical equipment 208 may comprise, for example, one or more devices located proximate to a patient. In an embodiment, the medical equipment interacts with a base station using a communications network such as a LAN, as described above. Either a single LAN may be used, with one or more devices communicating with the base station using a single communications network, or multiple LANs may be used, with each allowing one or more devices to communicate with the base station. Alternatively, in an embodiment, the medical equipment 208 interacts directly with a remotely located server 102 or other computing device using a WAN 103.

In a preferred embodiment, the medical equipment communicates with a base station using a LAN with the ZigBee specification. ZigBee allows for the creation of a local area network using small, low-powered digital radios. ZigBee is secured by symmetric encryption keys, allowing for the transmission of encrypted data. In an embodiment, the base station serves as the coordinator of the ZigBee network, with each of the associated devices acting as nodes. The network may be structured in a star configuration (wherein each medical device communicates directly with the base station), a tree configuration (wherein some medical devices communicate with each other while others communicate directly with the base station), a mesh configuration (wherein each medical device communicates with every other medical device and the base station), or in another suitable configuration, as recognized by one of skill in the art.

As shown in FIG. 3, in an embodiment, the devices include: a height-measuring unit 302; ultrasound/Doppler probes 304; a stethoscope 306; a microscope 308; a temperature measuring unit 310; a pulse oxidation ("pulse ox") measuring unit 312; a weight measurement unit 314; a sensor 316 to analyze blood so as to measure troponin, complete blood count ("CBC"), and/or electrolytes in the blood and/or to detect congestive heart failure and fluid retention; a blood pressure (BP) measuring unit 318; a fundus camera 320; an electrocardiograph ("ECG" or "EKC") 322; and an ophthalmoscope 324. As will be understood by one of skill in the art, other medical devices may also be adapted for use in a system in accordance with the present invention.

Generally speaking, any medical device may be adapted to work with a system in accordance with the present invention by supplying it with an appropriately configured adapter, such as the adapter discussed below. Additionally, particular embodiments of specialized medical devices designed to operate with a system in accordance with an embodiment of the present invention are discussed below.

Height Unit

Figure 4:
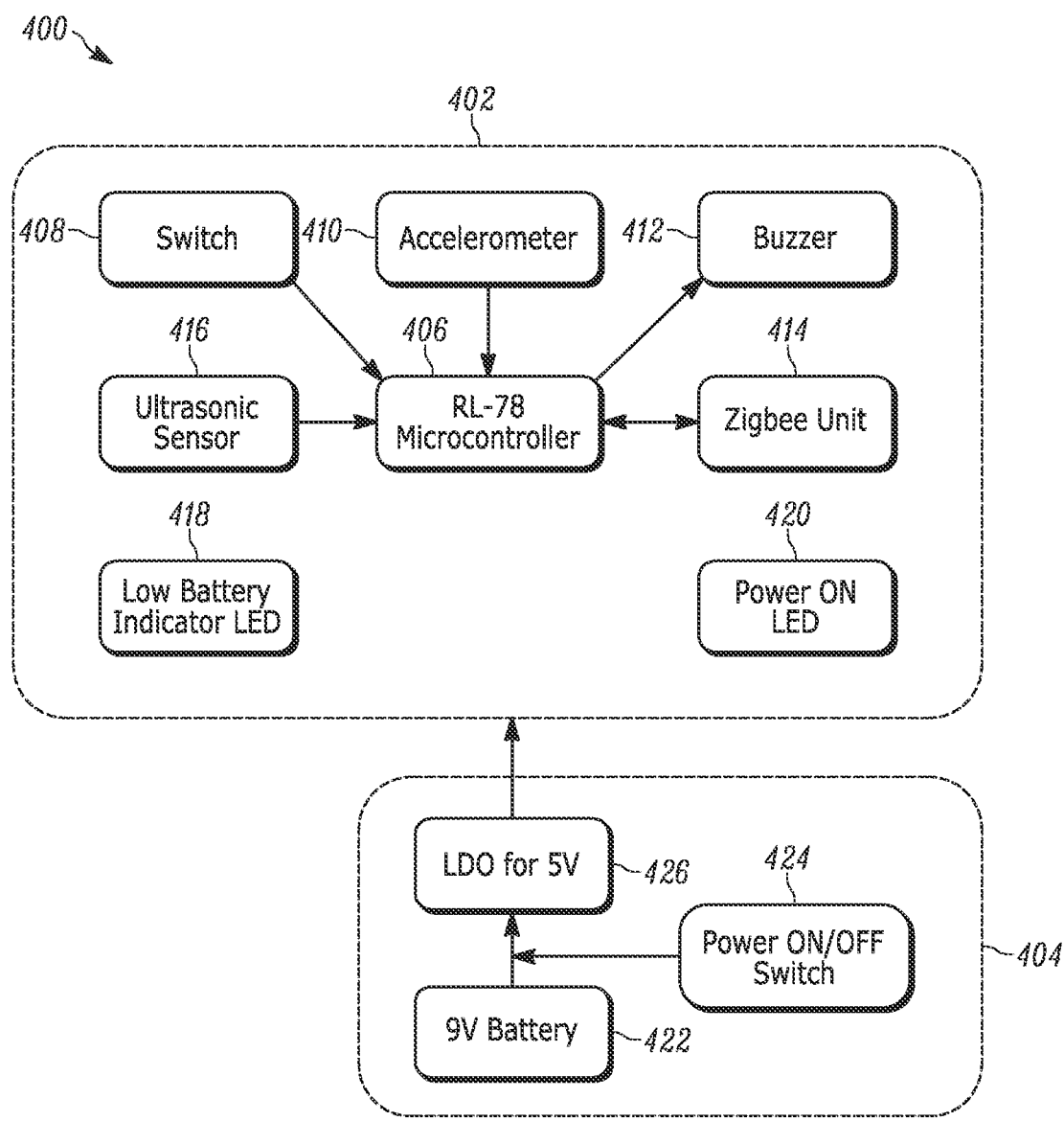
FIG. 4 depicts a block diagram of a height measuring unit in accordance with an embodiment of the present invention.

A device for measuring the height of a person (a "Height Unit"), such as a patient, for use in a system in accordance with an embodiment of the present invention will now be discussed. With reference to FIG. 4, a block diagram illustrating component parts of a Height Unit 400 is shown. In an embodiment, the Height Unit 400 comprises a microcontroller 406, such as an RL-78 microcontroller. In an embodiment, the microcontroller 406 is attached to an input device 408 (such as a switch), an accelerometer 410, an output device 412 (such as a buzzer), a communications unit 414 (such as a ZigBee unit), and an ultrasonic sensor 416. The Height Unit 400 may also include a low battery indicator 418 and a power-on indicator 420. These indicators 418, 420 may be in the form of light emitting diodes ("LEDs").

In an embodiment, the Height Unit 400 comprises a power supply 404. In an embodiment, the power supply 404 is separate from the main body 402 of the Height Unit 400. In an embodiment, the power supply 404 comprises a battery 422 and a power switch 424 configured to disconnect the battery from the main body 402 of the Height Unit 400. In an embodiment, the battery 422 is a nine-volt (9V) battery. In an embodiment, the power supply 404 further comprises a low-dropout ("LDO") regulator 426 which provides a minimum voltage supply to the Height Unit 400, such as a five-volt (5V) supply.

In an embodiment, the battery 422 is a rechargeable battery (e.g., a lithium-ion battery) of approximately 3,500 mAH. Such a battery 422 will provide approximately 7-8 hours of uninterrupted operation. The capacity of the battery 422 may be increased to provide additional operational hours needed without recharging.

In an alternative embodiment, the Height Unit 400 is powered by an alternating current (AC) power supply rather than a battery 422. In an embodiment, the Height Unit converts the AC signal to a direct current (DC) signal using an AC/DC converter. In an embodiment, the power switch 424 is connected so as to disconnect the main body 402 of the Height Unit 400 from the power supply 404.

In an embodiment, the switch 408 attached to the microcontroller 406 enables manual control of the Height Unit 400 by an individual in physical proximity to the Height Unit 400. For example, a nurse may cause the Height Unit 400 to begin collecting measurements by flipping the switch 408.

In an embodiment, the ultrasonic sensor 416 is used to measure the distance between the Height Unit 404 and the floor. By holding the Height Unit 400 level and even with the top of a patient's head, the height of the patient may be determined. In an embodiment, the Height Unit 400 uses the accelerometer 410 to determine when the Height Unit 400 is level, thereby preventing incorrect measurements from being obtained.

Figure 5B:
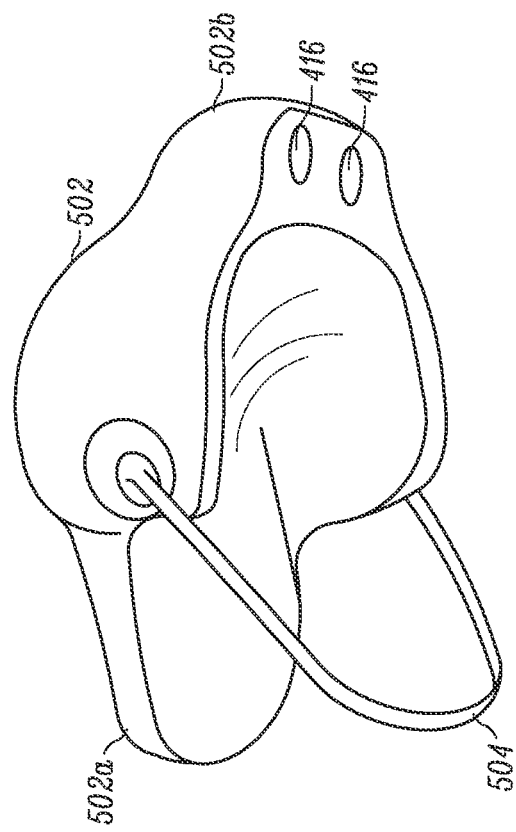
FIGS. 5a and 5b depict profile views of a first height measuring unit in accordance with an embodiment of the present invention.
Figure 5A:
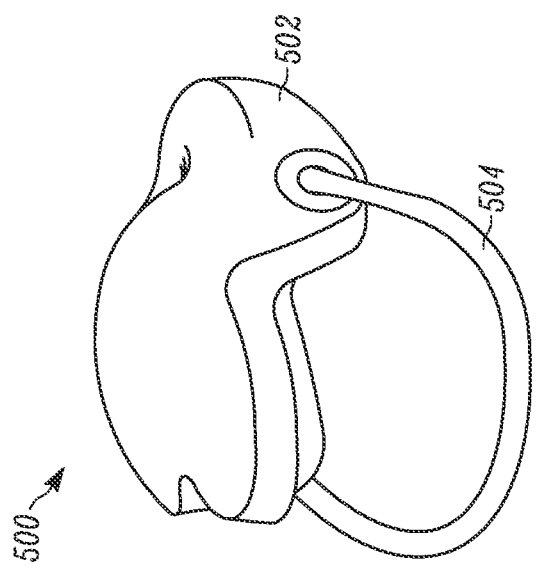

As shown in FIGS. 5a and 5b, in an embodiment, a Height Unit 500 comprises a body 502 sized so as to fit on a person's head. A chin strap 504 is attached to the body 502 and is configured so as to secure the Height Unit 500 on a person's head. The body 502 comprises a protrusion 502a located at the forward end of the Height Unit 500. A rear portion 502b is located on the body 502 opposite the protrusion 502a and holds a plurality of downward-facing ultrasonic sensors 416. In an embodiment, the body 502 is configured to house one or more accelerometers 410, ultrasonic sensors 416, the microcontroller 406, the ZigBee module 414, and the power supply 404. In an embodiment, the indicators 418, 420, and switch 408 are mounted on the exterior surface of the body 502.

As shown in FIGS. 5a and 5b in an embodiment, the protrusion 502a extends laterally from the body 502. In use, the interior surface of the body 502 rests against the highest portion of a patient's head. The body 502 is thereby positioned next to the patient's head. When the one or more accelerometers 410 indicate that Height Unit 500 is held level, that is, held so that the protrusion 502a is substantially parallel to the floor, the microcontroller 406 uses the plurality of ultrasonic sensors 416 to measure the distance between the Height Unit 500 and the floor. If necessary, the microcontroller 406 can adjust the distance (e.g., by adding in the distance between the plurality of ultrasonic sensors 416 and the bottom surface of the protrusion 502a) so as to accurately determine the person's height. As will be clear to one of skill in the art, other methods may be used to calculate the height of a person using the one or more accelerometers 410 and the plurality of ultrasonic sensors 416 in the Height Unit 500.

In an embodiment, a buzzer, speaker, or other sound generating device 412 attached to the microcontroller 406 produces a sound to indicate that a height measurement has been successfully obtained. For example, one tone may sound to indicate that the Height Unit 500 is waiting to obtain a measurement until the Height Unit 500 is held level. A second tone may then play to indicate that the height measurement has been obtained.

Once the height measurement is obtained, the microcontroller 406 may then use the ZigBee module 414 (or another communication module) to communicate the measured height to the base station 106, the server 102, or directly to a physician located remotely from the Height Unit 500. In an embodiment, this communication occurs wirelessly. In an embodiment, the measurement is sent from the microcontroller 406 to a Single Board Controller ("SBC"). The SBC may be, by way of example and not limitation, a tablet PC such as portable tablet 112, a handheld device 111, a portable computer 113, or another computer 105 running a master program and located remotely from the Height Unit 500. There need not be any wired connection between the Height Unit 500 and the SBC and the signal may be transmitted using a communication network such as the network 103. As such, the Height Unit 500 may be operated by a remotely located physician.

Figure 6A:
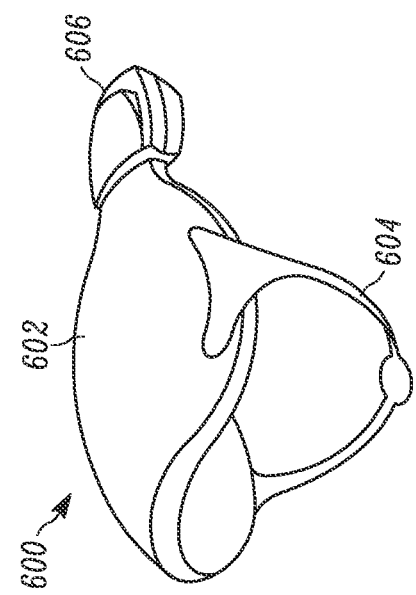
FIG. 6a depicts a profile view of a second height measuring unit with an arm in a retracted position in accordance with an embodiment of the present invention.
Figure 6B:
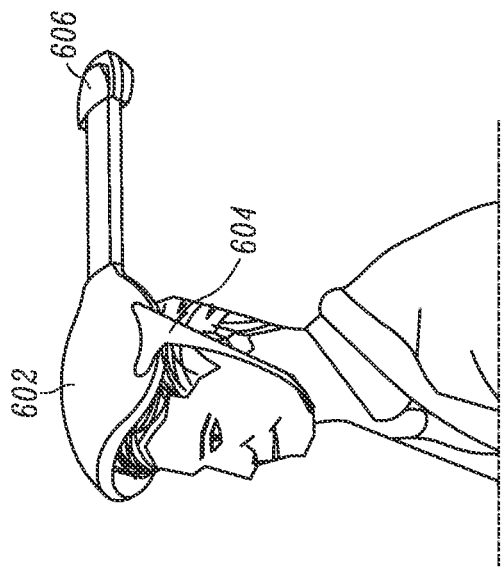
FIG. 6b depicts a profile view of the height measuring unit of FIG. 6a worn by a person with the arm in an extended position.

As shown in FIGS. 6a and 6b, in an embodiment, a Height Unit 600 comprises a body 602 attached to a chin strap 604 and an arm 606 which extends away from the rear of the body 602. The arm 606 is configured to hold the plurality of ultrasonic sensors 416 on a downward facing side thereof. In an embodiment, the arm 606 is configured to move between a retracted position (as shown in FIG. 6a) to an extended position (as shown in FIG. 6b). The extended position enables the plurality of ultrasonic sensors 416 to have an unobstructed path to the floor. In the retracted position, the arm 606 takes up less room so as to allow for easy storage and transportation of the Height Unit 600.

Figure 6C:
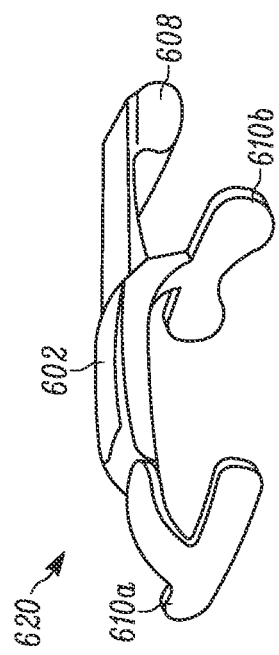
FIG. 6c depicts a profile view of a third height measuring unit in accordance with an embodiment of the present invention.
Figure 6D:
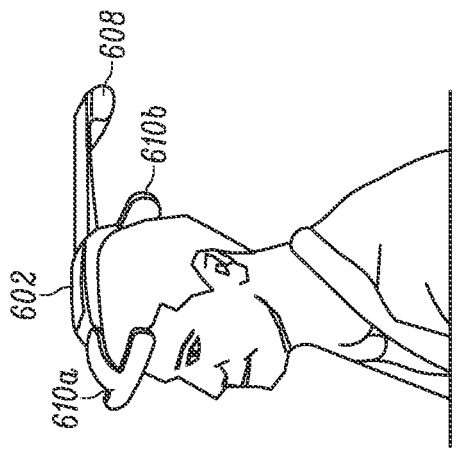
FIG. 6d depicts a profile view of the height measuring unit of FIG. 6c worn by a person.

As shown in FIGS. 6c and 6d, in an embodiment, a Height Unit 620 comprises a body with a forward support 610a and rearward support 610b and an arm 608 configured to hold the plurality of ultrasonic sensors 416 on a downward facing side thereof.

Weight Unit

Figure 7:
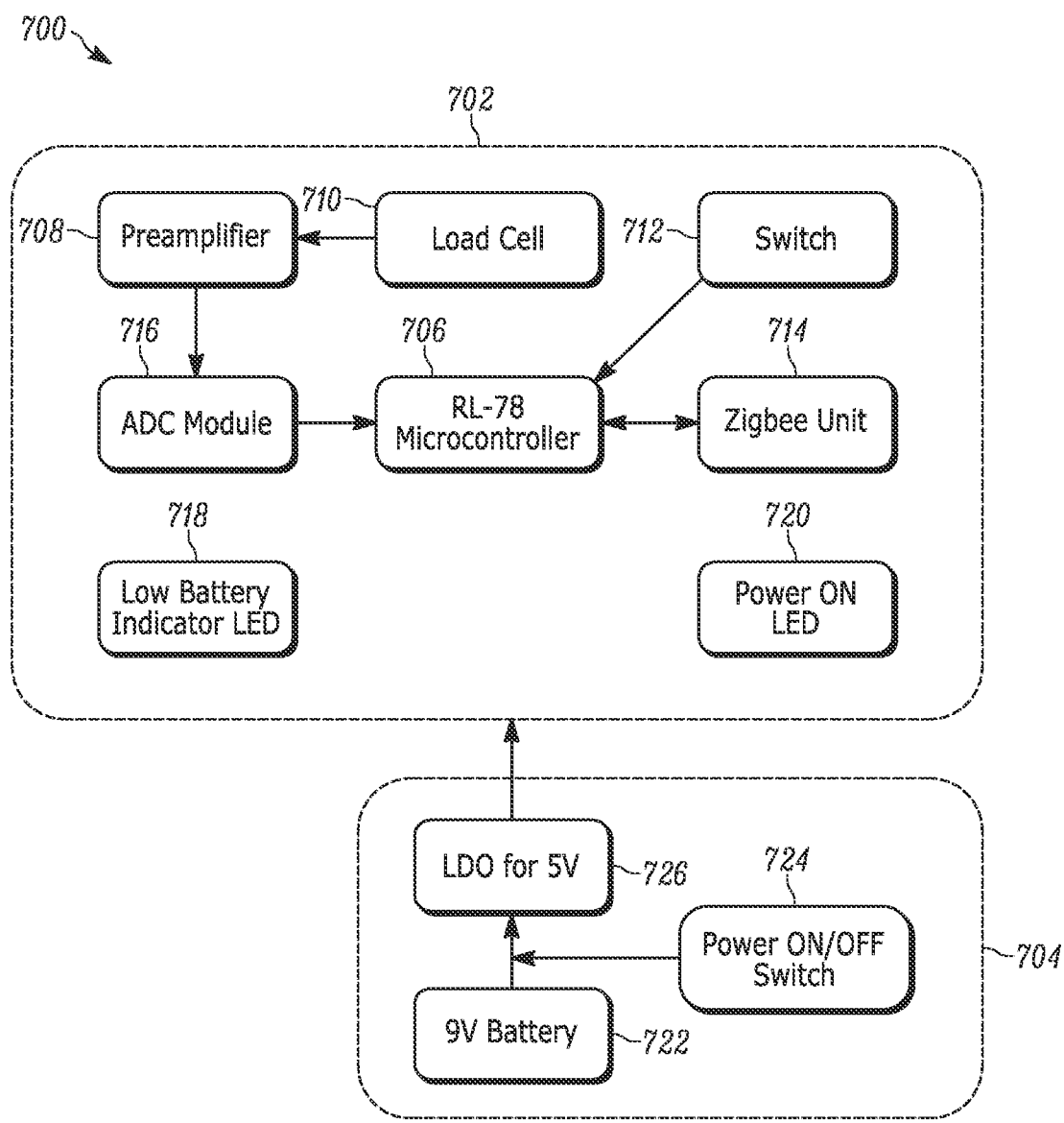
FIG. 7 depicts a block diagram of a weight measurement unit in accordance with an embodiment of the present invention.

A device for measuring the weight of a person (a "Weight Unit"), such as a patient, for use in a system in accordance with an embodiment of the present invention will now be discussed. With reference to FIG. 7, a block diagram illustrating component parts of a Weight Unit 700 is shown. In an embodiment, a Weight Unit 700 includes a microcontroller 706, such as an RL-78 microcontroller. In an embodiment, the microcontroller 706 is operatively connected to an input device 708 (such as a switch), an analog to digital converter (ADC) module 716, and a communications unit 714 (such as a ZigBee unit). The ADC module 716 may in turn be operatively connected to a preamplifier 712 (also termed a preamplification module or preamp), which in turn may receive the output from a weight-loading cell 710. The weight-loading cell 710 creates an analog output signal indicative of the amount of force applied to the cell 710. For example, the weight-loading cell 710 may include a strain gauge that deforms in a predictable fashion when subjected to a force, thereby reflecting the magnitude of the force applied to the strain gauge in the deformation of the gauge. This deformation is further reflected in the change in magnitude of an electrical signal; as the strain gauge deforms, the effective electrical resistance of a wire similarly changes, thereby generating an analog signal representative of the force. In an embodiment, four strain gauges may be used in a Wheatstone bridge configuration in a single load cell 710.

By having a patient stand on the weight-loading cell 710, an analog signal representative of the patient's weight may be obtained. This analog signal is magnified, if necessary, by the preamp module 712 and converted to a digital signal by the ADC module 716. The signal is then provided to the microcontroller 706, which may convert the signal into a number representing the person's weight and transmit that number to the base station, the server 102, or directly to a computing device in proximity to a remotely located physician using the communication module 714. Alternatively, the signal may be converted once it received by the base station 106, server 102, or other computing device in proximity to the remotely located physician. In an embodiment, the measurement is sent from the microcontroller 706 to an SBC. The SBC may be, by way of example and not limitation, a tablet PC such as portable tablet 112, a handheld device 111, a portable computer 113, or another computer 105 running a master program and located remotely from the Weight Unit 700. There need not be any wired connection between the Weight Unit 700 and the SBC and the signal may be transmitted using a communication network such as the network 103. As such, the Weight Unit 700 may be operated by a remotely located physician.

In an embodiment, a buzzer, speaker, or other sound generating device (not shown) may be attached to the microcontroller 706. In an embodiment, the buzzer is used to indicate that a weight measurement has been successfully obtained. For example, one tone may sound to indicate that the Weight Unit is waiting to obtain a measurement until a reliable reading can be saved. A second tone may then play to indicate that a measurement has been successfully obtained. In an alternative embodiment, another output device—such as a display—is used to provide feedback to a patient. In an embodiment, a display is operatively connected to the microcontroller 706 and displays a patient's weight visually.

In an embodiment, the Weight Unit 700 resolves a patient's weight in multiples of 10 grams with a minimum weight sensitivity of 500 grams and maximum capacity of 400 kilograms.

In an embodiment, the Weight Unit 700 comprises a power supply 704 and a main body 702. In an embodiment, the Weight Unit is battery powered and the power supply 704 comprises a battery 722 (such as a 9V battery), a power switch 724, and an LDO 726. In an embodiment, the battery 722 is a rechargeable battery (e.g., a lithium-Ion battery) of approximately 3,500 mAH. Such a battery will provide approximately 7-8 hours of uninterrupted operation. The capacity of the battery 722 may be increased to provide additional operational hours needed without recharging. In an embodiment, the Weight Unit 700 includes a low battery indicator 718 and a power-on indicator 720. These indicators 718 720 may be in the form of light emitting diodes, or LEDs. In an embodiment, the battery 722 is a nine-volt battery and the low-dropout regulator (LDO) provides a minimum power supply, such as a five-volt supply, to the Weight Unit 700. In an embodiment, the power switch 724 is configured so as to connect or disconnect the power supply 704 from the main body 702.

In an alternative embodiment, the Weight Unit 700 may be powered by a standard AC power supply. The Weight Unit may convert the AC signal to a DC signal using a standard AC/DC converter. A power switch may be connected so as to disconnect the Weight Unit from the power supply.

In an embodiment, the Weight Unit 700 comprises a housing with a lower horizontal plate separated from an upper horizontal plate. The load cell 710 is located therebetween, such that when a patient steps onto the upper horizontal plate, force is transferred from the upper horizontal plate through the load cell to the lower horizontal plate and the floor.

In an embodiment, the Weight Unit 700 is configured such that a mechanical frame may be removably attached to the Weight Unit 700. By way of example, the mechanical frame may be removably attached to the upper horizontal plate. In an embodiment, the mechanic frame is configured to removably hold a baby-carrier or other baby-holding mechanism. By first measuring the weight of the mechanical frame and baby-carrier alone before measuring the weight of these items with an infant placed in the baby-carrier, the Weight Unit may be used to accurately and easily determine the weight of an infant.

Stethoscope

A specialized stethoscope (Stethoscope Module) for use in a system in accordance with an embodiment of the present invention will now be discussed.

As is known by one of skill in the art, a stethoscope is an acoustic medical device for listening to the internal sounds of a human body. A stethoscope may be analog and transmit sound acoustically between a bell and one or more earpieces, for example, by utilizing a series of hollow air-filled tubes to carry the sound. Alternatively, a stethoscope may be electronic and convert the acoustic sound waves into electrical signals. Embodiments of the present invention may use either design.

Figure 8:
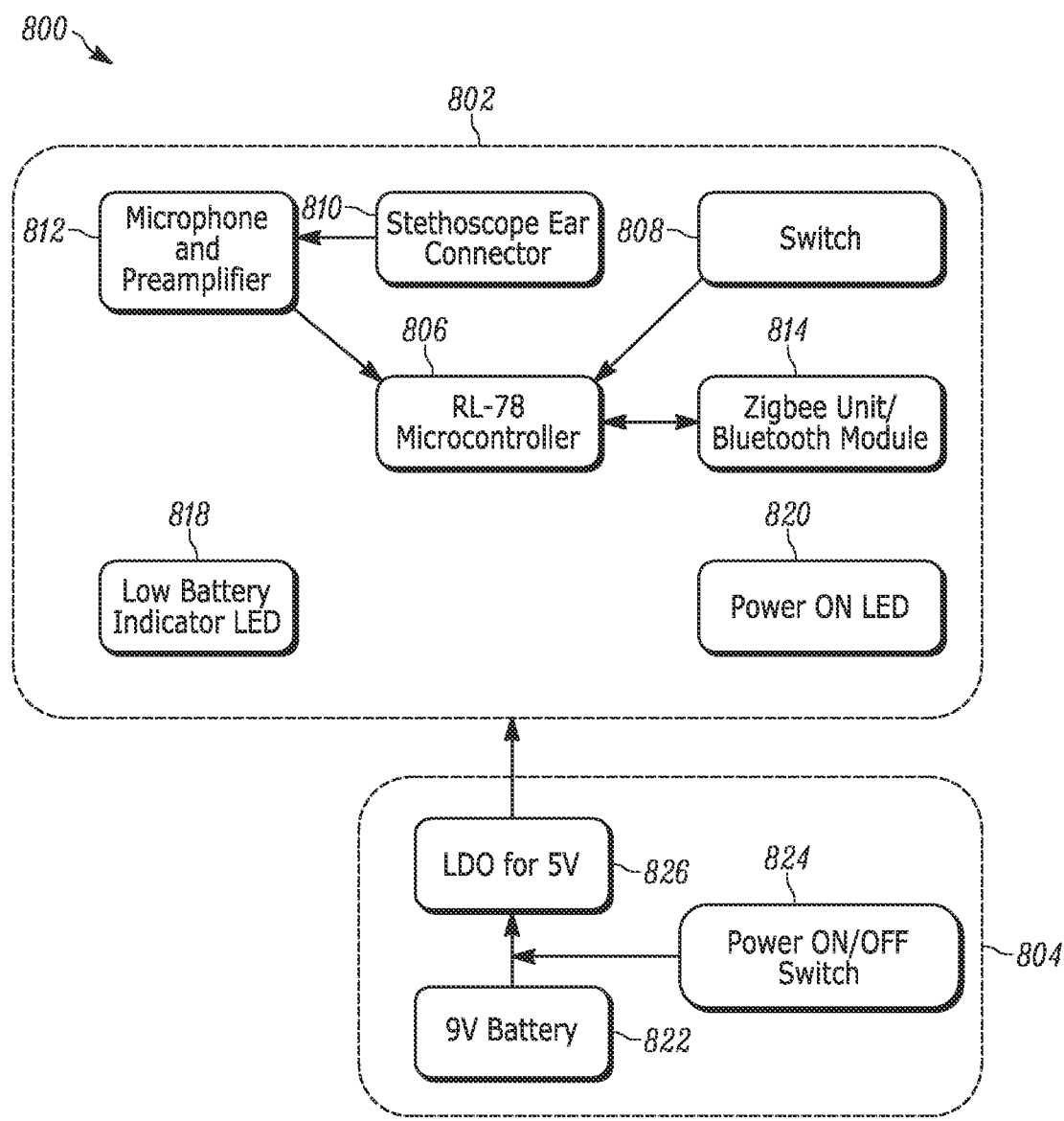
FIG. 8 depicts a block diagram of a portion of a stethoscope unit in accordance with an embodiment of the present invention.

With reference to FIG. 8, a block diagram illustrating component parts of a Stethoscope Module 800 is shown. The Stethoscope Module 800 connects to the ear connector(s) 810 of a standard acoustic stethoscope or electronic stethoscope. Alternatively, in an embodiment, the Stethoscope Module 800 is configured to directly receive an electrical signal from an electronic stethoscope. In an embodiment, the Stethoscope Module 800 includes a microcontroller 806, such as an RL-78 microcontroller. In an embodiment, the microcontroller 806 is operatively connected to an input device 808 (such as a switch), a communication module 814, and a microphone/preamplifier module 812. Alternatively, in an embodiment, the microcontroller 806 is directly connected to an electronic stethoscope and receives an electrical signal therefrom The microphone input and preamp module receives the input from a stethoscope ear connector. In an embodiment, the communication module 814 is a Bluetooth module containing a transceiver for communicating with another remotely located transceiver utilizing the Bluetooth protocol.

In an embodiment, the Stethoscope Module 800 is wirelessly connected to a stethoscope, for example through the use of the communication module 814. In an embodiment, the communication module 814 comprises a Bluetooth transceiver which allows the Stethoscope Module to be located remotely from the stethoscope. For example, the majority of the Stethoscope Module may be stored in a backpack or worn on a strap around an individual's neck. A small subunit containing a Bluetooth transceiver and the microphone input and preamp module may be plugged into the stethoscope's earpiece so as to allow the Stethoscope Module 800 to receive and transmit sounds from the stethoscope to the base station 106, the server 102, or another computing device such as a computing device located proximate to a remotely located physician.

In the case of an acoustic stethoscope, the microphone input and preamp module 812 is configured to include a microphone to convert the acoustic sound waves into electrical signals. The preamplifier 812 is configured to amplify the electrical signals as needed prior to transmitting the signals via the Bluetooth module to the microcontroller. In an embodiment, the microphone input and preamp module 812 is configured to directly receive the electrical signals output by an electric stethoscope. In an embodiment, the preamplifier is configured to boost the electric signals prior to relaying them to the microcontroller 806.

In an embodiment, the Stethoscope Module 800 is located in close proximity to the stethoscope. In such an embodiment, as shown in FIG. 8 the microphone input and preamp unit 812 may be directly connected to the microcontroller 806, without utilizing the communication module 814.

In an embodiment, the Stethoscope Module 800 comprises a power supply 804 and a main body 802. In an embodiment, the power supply 804 comprises a battery 822. In an embodiment, the battery 822 is a rechargeable battery (e.g., a lithium-ion battery) of approximately 3,500 mAH. Such a battery will provide approximately 7-8 hours of uninterrupted operation. The capacity of the battery 822 may be increased to provide additional operational hours needed without recharging. The Stethoscope Module 800 may also include a low battery indicator 818 and a power-on indicator 820. These indicators 818 and 820 may be in the form of light emitting diodes, or LEDs.

In an embodiment, the power supply 804 comprises a nine-volt battery 822 coupled to a low-dropout regulator (LDO) 826 which provides a minimum power supply, such as a five-volt supply, to the main body 802. In an embodiment, a power switch 824 is connected so as to disconnect the battery and the LDO from the main body 802. In an alternative embodiment, the Stethoscope Module comprises a standard AC power supply. The power supply 804 converts the AC signal to a DC signal using a standard AC/DC converter. In an embodiment, a power switch 824 is connected so as to disconnect the main body 802 of the Stethoscope Module 800 from the power supply 804.

Figure 9B:
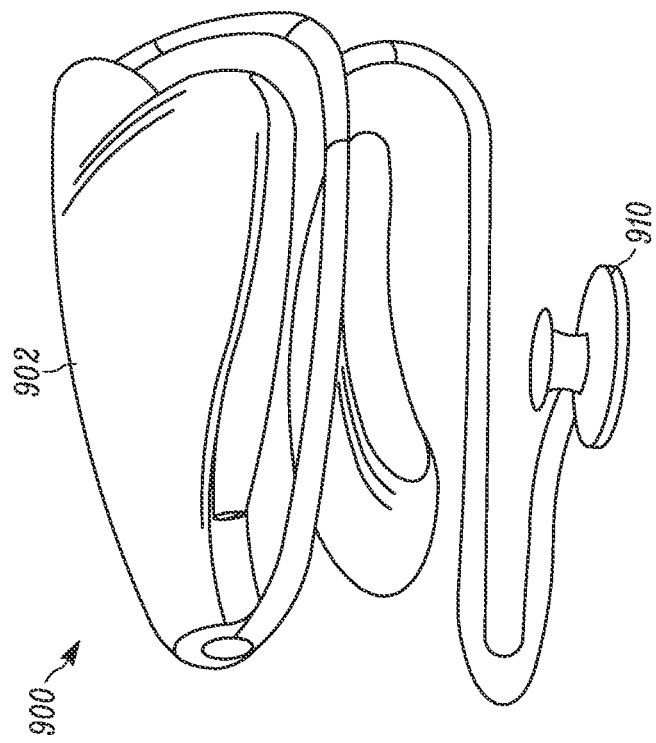
FIG. 9b depicts a profile view of the stethoscope unit of FIG. 9a with the stethoscope attached in accordance with an embodiment of the present invention.
Figure 9A:
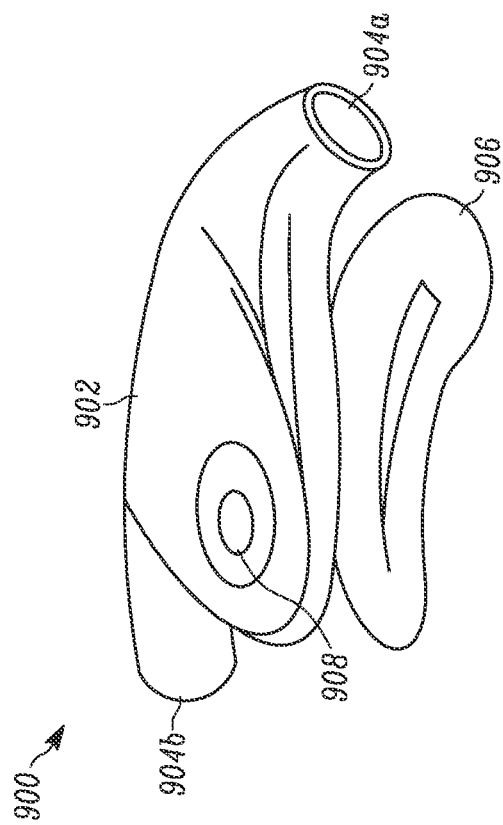
FIG. 9a depicts a profile view of a stethoscope unit with the stethoscope removed in accordance with an embodiment of the present invention.

As shown in FIG. 9a, in an embodiment, a Stethoscope Module 900 comprises a body 902 with a pair of ear connectors 904a and 904b, each disposed on an end of the body 902. In an embodiment, the body 902 is supported by a stand 906. In an embodiment, the components of the Stethoscope Module 800 are housed within the body 902. In an embodiment, the body 902 includes a diaphragm 908 centrally disposed on the body 90 for recording a patient's heartbeat without the use of a separate stethoscope. The diaphragm 908 is operatively connected to the microcontroller 806. In use, the Stethoscope Module 900 is held such that the diaphragm is proximate to a patient's chest. By measuring small changes in air pressure, the diaphragm 908 may record the patient's heartbeat. Alternatively, a standard stethoscope may be employed by placing the stethoscope's earpieces proximate to the ear connectors 904a and 904b.

As shown in FIG. 9b, once the stethoscope 910 is properly connected to the Stethoscope Module 900, the stethoscope may be used as usual.

In an embodiment, a buzzer, speaker, or other sound generating device (not shown) may be operatively attached to the microcontroller 806 and configured to produce a sound to indicate that a measurement has been successfully obtained. For example, one tone may sound to indicate that the Stethoscope Module 800 is ready to obtain a measurement. A second tone may then play to indicate that the Stethoscope Module 800 has successfully obtained a measurement and may be removed from a patient's chest.

Medical Device Adapter

An adapter for using a standard medical device with a system in accordance with an embodiment of the present invention will now be discussed. In an embodiment, the adapter 1000 is connected to a standard or off the shelf medical device (not shown), such as by way of example and not limitation, a pulse oxidizer, a stethoscope, a scale, an EKG, a blood pressure monitor, or another medical device. The adapter 1000 then relays information produced by the medical device to another device, such as a base station 106. In an embodiment, the adapter 1000 relays information directly to a computing device 104 located proximate to a physician. In an alternative embodiment, the adapter relays information indirectly, such as through a base station 106, server 102, or another intermediary device.

In an embodiment, the adapter 1000 receives commands from another device, such as the base station 106, a server 102, or another device such as a computer device located proximate to a physician. In an embodiment, the adapter 1000 comprises an output module (not shown) operatively connected to the medical device and controls the operation of the standard medical device to which it is attached based on the received commands. In this way, the adapter effectively allows a remotely located user (such as a physician) to receive the information produced by the medical device and control the medical device, just as if the physician were physically located proximate to the medical device.

In an embodiment, the adapter 1000 includes a microcontroller 1006, such as an RL-78 microcontroller. The microcontroller 1006 governs the operation and functioning of the adapter 1000. In an embodiment, the microcontroller 1006 is attached to a communications unit 1014 (such as a ZigBee and/or Bluetooth module). The communications unit 1014 enables communication between the adapter 1000 and the base station 106 or other computing devices. In an embodiment, the adapter 100 includes an input device or sensor 1010 which is configured to receive information from a particular medical device. For example, the input device 1010 may comprise a microphone, a camera, a pressure sensor, or an input terminal for receiving an electrical signal either wirelessly or via one or more wires. In an embodiment, the adapter 1010 includes an output device (not shown) which is configured to provide commands to a particular medical device. For example, the output device may comprise one or more servomotors or other actuators, a speaker, or an output terminal for outputting an electrical signal either wirelessly or via one or more wires. In an embodiment, the adapter includes a manual input device (not shown), such as, for example, a switch, keyboard, mouse, or touchscreen. In an embodiment, the manual input device allows an individual located in proximity to the adapter 100 to interact with the adapter 1000. For example, a first position of a switch may indicate that the adapter 1000 should begin communicating with the base station 106.

In an embodiment, the adapter 1000 comprises a display, such as a liquid crystal display (LCD) 1002. In an embodiment, the LCD 1002 is used to display information to a user of the adapter 1000.

In an embodiment, the adapter 1000 includes a power supply 1004 and a main body 102. In an embodiment, the adapter is battery powered. In an embodiment, a rechargeable battery (e.g., a lithium-ion battery) of approximately 3,500 mAH is used. Such a battery will provide approximately 7-8 hours of uninterrupted operation. The capacity of the battery may be increased to provide additional operational hours needed without recharging. The adapter 1000 may also include a low battery indicator 1016 and a power-on indicator 1018. These indicators 1016 and 1018 may be in the form of light emitting diodes, or LEDs. In an embodiment, the power supply 1004 comprises a nine-volt battery coupled to a low-dropout regulator (LDO), which provides a minimum power supply, such as a five-volt supply, to the main body 1002 of the adapter 1000. In an embodiment, a power switch is connected so as to disconnect the battery and the LDO. In an alternative embodiment, the power supply 1004 is a standard alternating current (AC) power supply. The power supply 1004 converts the AC signal to a direct current (DC) signal using a standard AC/DC converter. In an embodiment, a power switch is connected so as to disconnect the adapter from the power supply.

For example, an adapter in accordance with an embodiment of the present invention may be configured to interact with a standard optical microscope. Such an adapter may include an input device comprising one or more cameras which are configured to interact with the eye pieces on the microscope and an actuator configured to adjust the position of a slide under the microscope's lens. By viewing images transmitted from the cameras and sending commands to the actuators, a remotely located physician may interact with the microscope just as if he were physically present.

Pulse Oximeter

A specialized pulse oximeter (referred to herein as a pulse oximeter or oximetry module) for use in a system in accordance with an embodiment of the present invention will now be discussed.

As is known by one of skill in the art, pulse oximetry is a non-invasive method for measuring a person's oxygen, or $O_2$, saturation. Pulse oximetry measures the wavelengths of light that are preferentially absorbed by either oxyhemoglobin or deoxyhemoglobin. Pulse oximetry may be performed using either transmissive pulse oximetry or reflectance pulse oximetry. To perform transmissive pulse oximetry, a sensor may be placed on a thin part of a person's body, such as the tip of a finger or an earlobe, opposite a light source. By passing light through the person's body and measuring the changes in absorption of various wavelengths of light, the person's $O_2$ saturation may be determined. For reflectance pulse oximetry, the sensor is placed adjacent to the light source and measures the wavelengths of backscattered light. Embodiments of the present invention may use either design.

Figure 10:
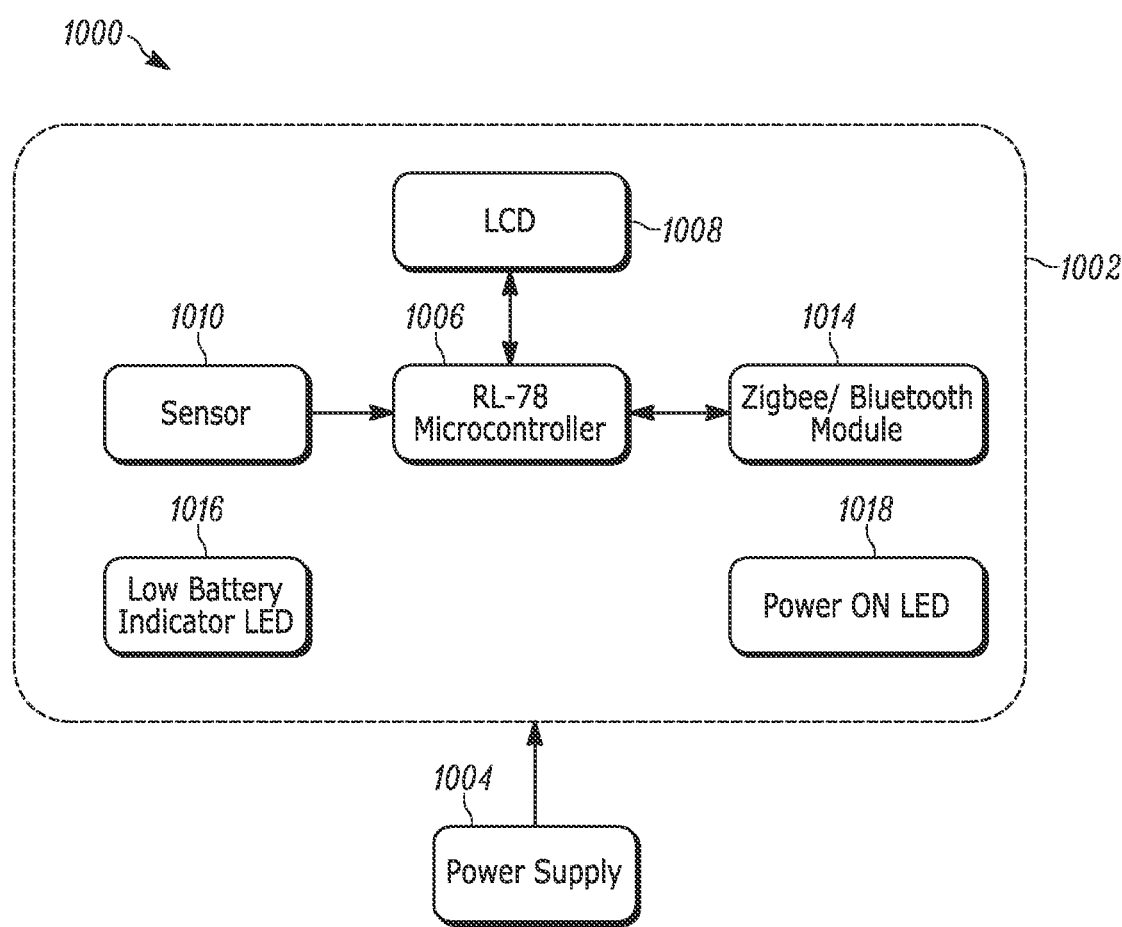
FIG. 10 depicts a block diagram of a pulse oximeter in accordance with an embodiment of the present invention.

With further reference to FIG. 10, in an embodiment, an Oximetry Module may include a structure similar to the adapter 1000 discussed above. In an embodiment, the Oximetry Module includes a microcontroller 1006, such as an MSP 430 microcontroller or a RL-78 microcontroller. In an embodiment, the microcontroller 1006 is attached to a display device 1008, such as a liquid crystal display (LCD) to display information to a person proximate to the Oximetry Module. The Oximetry Module may further include a wireless communication unit 1014 (such as a ZigBee unit). The microcontroller 1006 is connected to one or more light emitters and light sensors, such as an infrared ("IR") light emitter, a red light emitter, an IR light sensor and a red light sensor. In an embodiment, the IR emitter is configured to emit light at a wavelength of 660 nm and the IR emitter is configured to emit light at a wavelength of 940 nm. In an embodiment, a single photodiode is used to detect both IR and red light. In an embodiment, the light emitters are LEDs configured to cycle through a sequent IR LED on, red LED on, then both off at a rate of thirty times per second. In an embodiment, the emitter and sensor are arranged for transmissive oximetry. In an embodiment, the emitter and sensor are arranged for reflective oximetry. In an embodiment, a combined IR emitter/detector is used. In an embodiment, the IR emitter and detector are connected to the microcontroller via an h-bridge circuit. Based on the light detected by the IR emitter, the microcontroller may determine various information regarding a patient, such as the patient's $O_2$, saturation. This information may then be transmitted from the Oximetry Module to the base station, the server 102, or another computing device such as a computing device located proximate to a remotely located physician. Alternatively, the Oximetry Module may transmit the raw measurements obtained from the IR detector for later interpretation.

In an embodiment, the Oximetry Module is battery powered. A rechargeable battery (e.g., a lithium-ion battery) of approximately 3,500 mAH may be used. Such a battery will provide approximately 7-8 hours of uninterrupted operation. The capacity of the battery may be increased to provide additional operational hours needed without recharging. The Oximetry Module may also include a low battery indicator and a power-on indicator. These indicators may be in the form of light emitting diodes, or LEDs. Power may be supplied to the Oximetry Module by a nine-volt battery coupled to a low-dropout regulator (LDO), which provides a minimum power supply, such as a five-volt supply, to the adapter. A power switch may be connected so as to disconnect the battery and the LDO. In an alternative embodiment, the Oximetry Module may be powered by a standard AC power supply. The Oximetry Module may convert the AC signal to a DC signal using a standard AC/DC converter. A power switch may be connected so as to disconnect the Oximetry Module from the power supply.

In an embodiment, the measurement is sent from the microcontroller to a Single Board Controller ("SBC"). The SBC may be, by way of example and not limitation, a tablet PC such as portable tablet 112, a handheld device 111, a portable computer 113, or another computer 105 running a master program and located remotely from the Oximetry Module. There need not be any wired connection between the Oximetry Module and the SBC and the signal may be transmitted using a communication network such as the network 103. As such, the Oximetry Module may be operated by a remotely located physician.

In an embodiment, the Pulse Oximeter comprises a body configured to surround a patient's finger. A first portion of the body is placed beneath the patient's finger and a second portion of the body is placed above the patient's finger. The two portions are joined by a hinge which is spring loaded so as bias the two portions together. In an embodiment, the light emitters are located on the first portion facing the light sensors located on the second portion opposite thereto. In an alternative embodiment, the body comprises a single portion which may be held against a patient's skin. The light emitters and light sensor are located adjacent to one another.

BP Measurement Unit

A specialized blood pressure (BP) monitoring unit (referred to as a "BP Unit," a "BP Measurement Unit" herein) for use in a system in accordance with an embodiment of the present invention will now be discussed.

A blood pressure meter or sphygmomanometer is a device used to measure a person's blood pressure. A blood pressure monitor is generally comprised of an inflatable cuff which is placed around a patient's arm. An automatic pump increases the pressure in the cuff and restricts the blood flow through the patient's arm. A sensor in the meter measures the pressure in the cuff. Typically, the meter records the pressure at which blood flow (i) just begins flowing through the arm and (ii) flows unimpeded. In use, the cuff is placed smoothly and snugly around the patient's upper arm, at roughly the same vertical height as the patient's heart while the patient is seated with his or her arm supported. The cuff must be appropriately sized for the patient; if the cuff is too loose, the meter will register an incorrect low pressure while if the cuff is too tight, the meter will register an incorrectly high pressure. A blood pressure measurement may include both the systolic pressure, or pressure in a person's arteries when his or her heart beats (e.g., contracts) and the diastolic pressure, or pressure in the person's arteries between heartbeats (e.g., while the heart relaxes).

With further reference to FIG. 10 and the associated description above, in an embodiment, the electronics contained in a BP Unit are generally similar to those in the adapter 1000. In an embodiment, the sensor 1010 comprises a pressure gauge configured to measure the pressure in a cuff. In an embodiment, the sensor 1010 further comprises a transducer configured to measure vibrations in the cuff.

Figure 11:
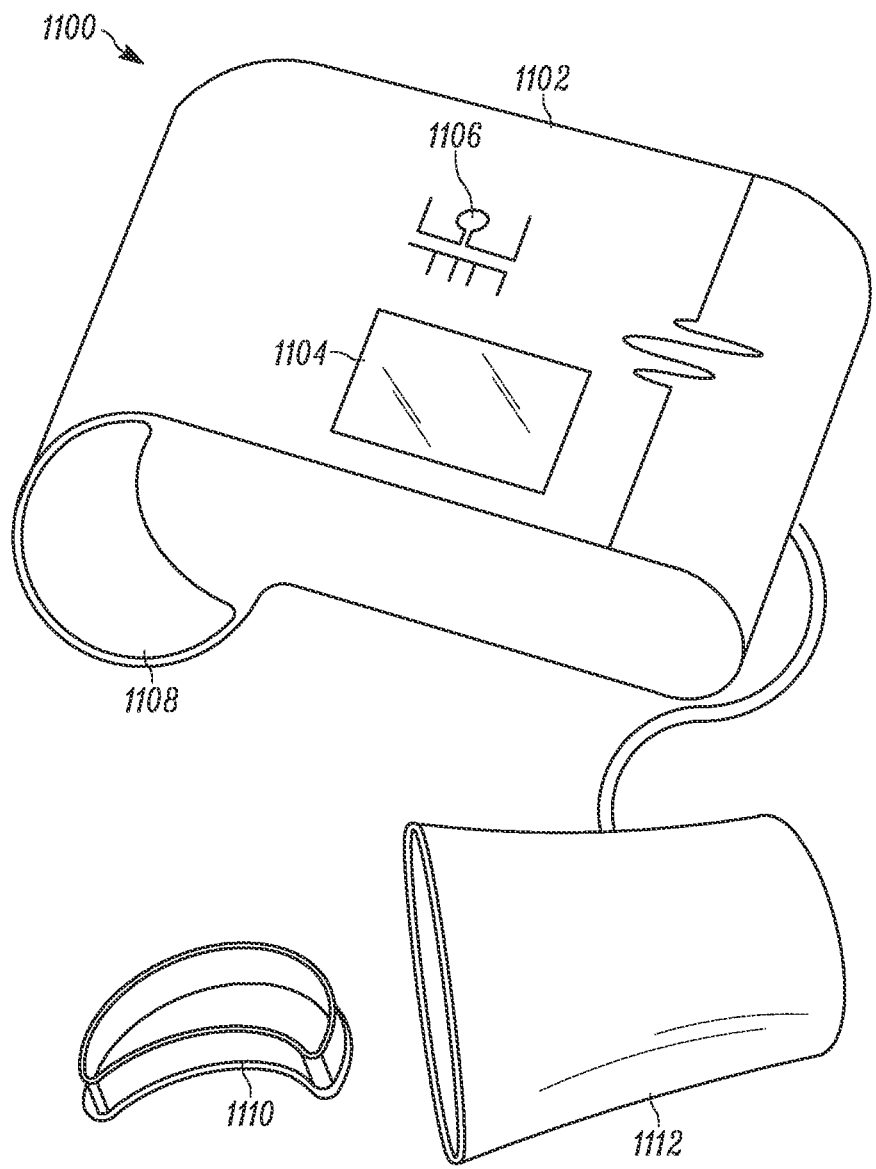
FIG. 11 depicts a profile view of a BP measurement unit in accordance with an embodiment of the present invention.

As shown in FIG. 11, in an embodiment, the BP Unit 1100 comprises a housing 1102 including a display 1104, an input device 1106, a storage compartment 1108 which may be sealed with a cover 1110, a pump and a pressure gauge (located within the housing 1102). The BP Unit 1100 further comprises a cuff 1112 which may be held in the storage compartment 1108 while not in use. In an embodiment, the cuff 1112 is removable from the BP Unit 1100 and may be replaced with a cuff 1112 of a different size so as to ensure the cuff 1112 is properly sized for a particular patient. In an embodiment, the BP Unit 1100 further comprises a transducer or oscillometer (not shown) located in the cuff 1112 and configured to generate a signal representative of the vibrations in the cuff 1112 and enable the determination as to whether blood is flowing through arteries in patient's arm.

In an embodiment, BP Unit 1100 is operated by wrapping the cuff around a patient's upper arm. In an embodiment, a signal provided by the input device 1106 indicates that the BP Unit 1100 should begin taking measurements. The pump increases the pressure in the cuff 1112 until the microcontroller determines that the pressure in the cuff has reached a target level, before gradually decreasing the pressure in the cuff while the pressure gauge records the pressure in the cuff 1112. In an embodiment, the target pressure is approximately 20 mm Hg above systolic pressure for the patent. In an embodiment, the display 1104 graphically displays the current blood pressure reading, along with an indication as to whether the measurement is complete. In an embodiment, the display 1104 provides simultaneous readout of systolic/diastolic pressure and pulse rate. In an embodiment, the BP Unit 1100 provides an alerts to the user if it detects an irregular heart beat.

Other Medical Devices

As will be understood by one of skill in the art, other specialized medical devices may be adapted for use with a system in accordance with an embodiment of the present invention, either by creating a specialized version of the medical device or through the use of an adapter, as described above. Additional medical devices, including but not limited to those shown in FIG. 3, are also contemplated.

Room Automation

Equipment will now be discussed for automating a patient's environment, such as a patient's room, for use in a system in accordance with an embodiment of the present invention.

Many variables relating to a patient's environment can typically be controlled by a physician located proximate to a patient, particularly in a controlled setting such as a hospital room. The intensity of the lights, the temperature of the room, the position of the bed, and other sources of noise such as a television (TV), fan, or air conditioning unit may all be controlled by such a physician. However, these variables typically require adjustment by a person physically present in the room. Accordingly, a need exists for a physician located remotely from a patient to be able to exercise similar control using telemedicine. Further, in the event that a physician and a patient are interacting using videoconferencing as described herein, it is advantageous for the physician to be able to adjust the room conditions to create an optimal environment for such interaction. For example, it may be desirable to eliminate all sources of background noise and increase the intensity of the lighting for the duration of the videoconferencing. Such control is provided to a remotely located physician by room automation equipment, in accordance with an embodiment of the present invention.

In an embodiment, a system in accordance with the present invention interacts with standard room automation equipment to allow a remotely located individual to control the room's conditions. In an alternative embodiment, customized room automation equipment is provided.

Figure 12:
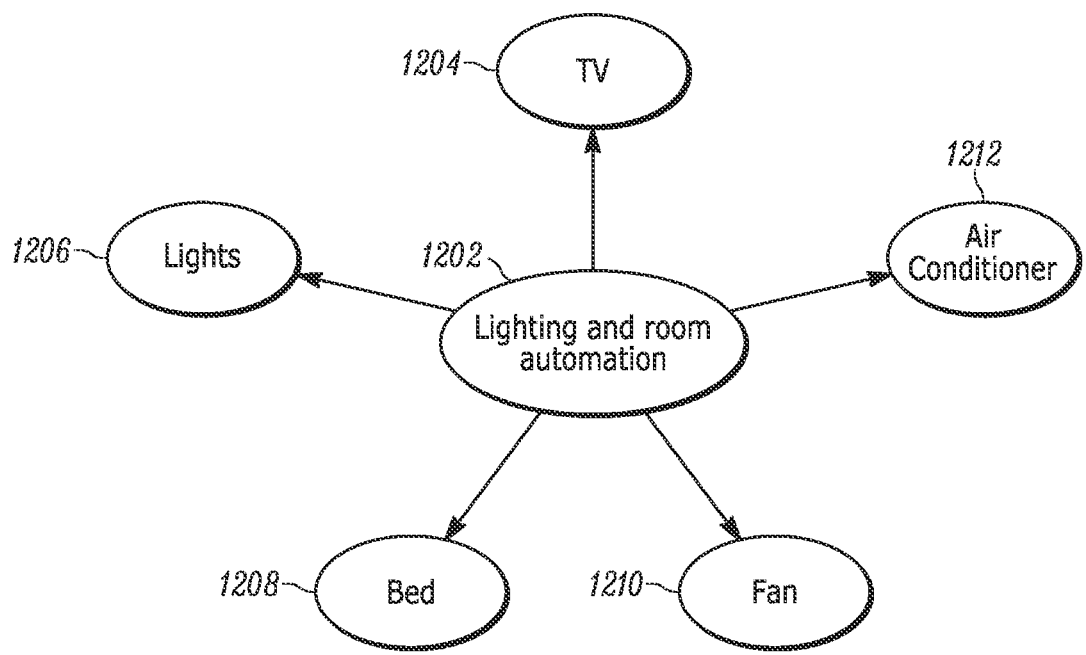
FIG. 12 depicts a block diagram of a system to automate control of the lights and other aspects of a room in accordance with an embodiment of the present invention.

With reference to FIG. 12, a block diagram illustrating several room automation modules is depicted. As shown in FIG. 12, in an embodiment, a lighting and room automation unit 1202 ("Automation Unit") controls a plurality of separate devices, including a television (TV) 1204 (using a TV Module), lighting 1206 (using a Lighting Module), a bed 1208 (using a Bed Module), a fan 1210 (using a Fan Module), and an air conditioner 1212 (using an Air Conditioning Module).

The Automation Unit 1202 may include a microcontroller and a communication unit, such as a ZigBee unit, to enable the Automation Unit 1202 to communicate with the base station 106, server 102, or other computing devices. The Automation Unit may include an additional one or more automation communication units adapted to communicate with the room automation equipment. For example, an automation communication unit may comprise an infrared (IR) emitter and/or receiver, thereby enabling interaction with a standard TV IR receiver without the need for a separate TV Module. Alternatively, an automation communication unit may comprise a wireless or wired transmitter, such as a ZigBee or Bluetooth unit. Each room automation device, such as the TV Module, Lighting Module, etc., may include a corresponding automation communication unit. In this way, the Automation Unit may communicate with each of the room automation devices directly. The Automation Unit may transmit information regarding the current conditions of the room, such as the lighting level, temperature, fan speed, and whether the TV is currently on and what channel is being watched. The Automation Unit may receive commands indicating changes that should be made to the room automation equipment, such as turning off the TV or reducing the fan speed. In an embodiment, the Automation Unit is incorporated into the base station.

The Lighting Control Unit 1206, for example, may include a microcontroller and an lighting control unit communicatively coupled with an automation communication unit in the main Automation Unit. In an embodiment, the Lighting Control Unit may further comprise a mechanism for adjusting the room lights, such as a dimmer switch connected in series with the room light's power supply. By adjusting the level of power supplied to the room lights, the level of light in the room may be controlled. As will be understood by one of skill in the art, similar devices may be used to control other systems in the room. In an embodiment, specialized devices (such as a specialized bed, TV, fan, etc.) comprise sensors, a microcontroller, and a communication unit and transmit the device's status and receive commands from the Automation Unit 1202.

Alarm and Patient Monitoring System

Equipment for monitoring a patient remotely for use in a system in accordance with an embodiment of the present invention will now be discussed.

Typically, a care provider such as a doctor or nurse must be physically present in a patient's room in order to monitor the patient. For example, it may be desirable to monitor whether a patient has moved or the status of a patient's vital signs. When a patient begins moving or has a significant change in status, a health care provider may need to take steps to adjust the patient's treatment or perform additional tests. In order to better enable treatment and monitoring by a remotely located physician, devices for monitoring a patient remotely are needed.

In an embodiment, a system in accordance with the present invention provides remote monitoring and automated alerts when a patient's status changes.

Figure 13:
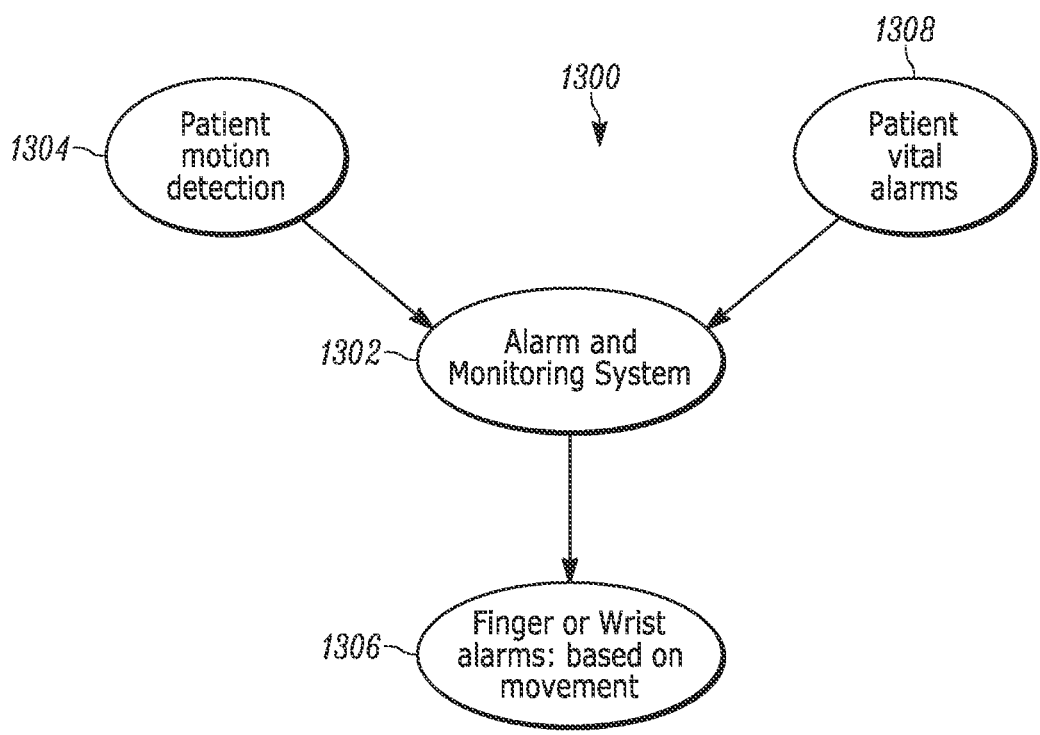
FIG. 13 depicts a block diagram of an alarm and monitoring system in accordance with an embodiment of the present invention.

With reference to FIG. 13, such an alarm and monitoring system may include several components to comprehensively monitor a patient's status. As shown in FIG. 13, the alarm and monitoring system 1300 may comprise a central controller 1302. In an embodiment, this controller is implemented in the base station. In an alternative embodiment, this controller is a separate piece of hardware and includes a microcontroller and at least one communication interface for interacting with other devices. The system 1300 may include one or more motion detectors 1304 to monitor patient movement. For example, a motion detector 1304 may include a sensor such as an IR sensor or an ultrasonic sensor to detect movement. Once movement is detected, the motion detector may notify the controller, which may then send an alert to the base station, a server 102, or another computing device. Alternatively, the motion detector may itself provide a notification. Such notification may be sent to a remotely located physician, for example, using the software as discussed herein, or may notify a health care provider in proximity to the patient.

Similarly, a sensor 1306 may be attached to a patient's body, such as a patient's wrist or fingers, so as to detect patient movements. In an embodiment, a sensor 1308 is configured to monitor a patient's vital signs, such as a patient's heartbeat, and provide an alert based on a change in patient status. Alternatively, standard medical equipment such as a heart rate monitor may be employed, with a device adapted to detect an alert such as an audible alert. Upon detecting an audible alert, a notification may be sent via the base station to the server 102 or a remote computing device. In an embodiment, a single device attached to a patient's wrist or finger comprises multiple sensors and is configured to monitor both movement and a patient's vital signs.

In an embodiment, an RFID tag is attached to a patient. Sensors are located in one or more locations; for example, sensors may be located in multiple rooms in a treatment facility. The RFID tag may be used to track a patient's movements through the treatment facility. In an embodiment, sensors are located at one or more pieces of medical equipment and are used to identify the patient being examined by the medical equipment. In an embodiment, RFID tags are attached to containers of medication and are used to track the location of the containers within the treatment facility.

By using monitoring and alarm systems in accordance with embodiments of the present invention, a single nurse or physician may monitor multiple patients at once.

Equipment Designs

Various examples of equipment designs in accordance with embodiments of the present invention will now be discussed. In an embodiment, the equipment such as the base station 106 is portable. The equipment be adapted to include a trolley or backpack so as to enable easy transportation.

A device may include one or more wheels to provide movement. These wheels may be operated by one or more servomotors, enabling the wheels to turn independently. Further, as shown in FIGS. 12-19, the device may include a camera, a microphone, a screen, and speakers. The device may be integrated with the base station described herein. The device may include one or more compartments to store additional devices, medications, or other objects. In an embodiment, the video camera may rotate independently and includes a zoom lens. The device may be controlled remotely, for example, by a physician using the GUI. Alternatively, the device may be automated or controlled by a program running on either the device or another computing device, such as the server 102.

The device may include a camera and screen. The device may include a height adjuster. The height adjuster may be located on the bottom surface of the device. The device may include an area for storage. The device may include lighting.

The device may be configured so as to fit into a backpack. The device may include a camera and a screen. While not in use, the camera and screen may be contained inside the device. The camera and screen may then fold out, be uncovered, or otherwise be removed from the device when in use. The device may include one or more compartments for storage. In an embodiment, the device is integrated into a backpack. The device may be configured to interact with one or more external add-on modules. These modules may increase the functionality of the device.

Software

Software for use with a system in accordance with embodiments of the present invention will now be discussed. As discussed herein, the software may run locally on one or more computing devices or may be transmitted to a computing device from a remote server. The software may enable communication using text, audio, and/or video between individuals located in separate locations. Further, the software may provide for the exchange of other information, such as images comprising the results of medical tests. In embodiment various embodiments, the software applications described herein may be implemented as instructions carried out by one or more hardware devices, as logical circuits or specialized hardware devices, or by any combination of the foregoing.

One aspect of software in accordance with an embodiment of the present invention is referred to herein as TiaImage™. In an embodiment, TiaImage™ includes a component running on a server 102 and a component running on a computing device, such as a tablet 112 or portable computer 113. In an embodiment, these components are stand-alone software components that run locally, such as an application (also known as an "App"). In an alternative embodiment, these components are run via the Internet using a protocol such as the World Wide Web.

In an embodiment, the TiaImage™ server component provides access to images, such as images created in the Digital Imaging and Communications in Medicine ("DICOM") format. As will be understood by one of skill in the art, DICOM provides both a file format and a communications protocol to enable medical information to be handled, stored, printed, and/or transferred. In an embodiment, the TiaImage™ server supports DICOM images including monochrome or color images with the color palette specified in RGB or YBR. In an embodiment, the TiaImage™ server supports multiple video and image formats, including DICOM files (used for test information such as that generated by MRI, CT or x-ray), JPEG, and MP4, among other formats.

In an embodiment, the DICOM files may be uploaded to the TiaImage™ server component from a variety of sources, including networked computing devices and the specialized medical equipment discussed above. In an embodiment, the TiaImage™ server component may check the credentials of users, for example, using the lightweight directory access protocol ("LDAP") or remote authentication dial in user service ("RADIUS") so as to ensure confidential information is only accessed by authorized users. In an embodiment, all information transmitted between the TiaImage™ server component and other components is encrypted so as to further protect confidential information in transit.

In an embodiment, the TiaImage™ server component includes lists of each user's favorite items and recently accessed items. In an embodiment, the TiaImage™ server component supports audit logging, particularly regarding doctor/patient interactions. In an embodiment, the TiaImage™ server component allows a user to access patient records using a name, an identification number such as a social security number ("SSN"), or other identifying information such as a patient's date of birth ("DOB"). In an embodiment, the TiaImage™ server component provides an information database listing health care providers, such as hospitals and clinics, as well as a list of doctors located at each location.

In an embodiment, the TiaImage™ user component may be accessed either using a local application or App on a device such as iPad, or using a web-based application, and interacts with the TiaImage™ server component running on one or more remote servers 102. In an embodiment, the TiaImage™ user component provides a welcome screen that provides a brief explanation of the software features available, lists a number of recently accessed options, and lists a number of features selected by a user, such as the user's favorite features. The TiaImage™ user component allows a user to access, view, and manipulate information such as DICOM files. For example, the TiaImage™ user component may display a DICOM image along with overviews, such as a ruler to indicate the scale of the image. Detailed image data may be presented. A user may compare multiple files side by side. In an embodiment, TiaImage™ allows users to access either a quick view or a detailed view of a file.

A related software component in accordance with an embodiment of the present invention, called TiaRecon™, may operate on a portable device such as a smartphone or iPhone. The TiaRecon™ software may contain features similar to TiaImage™. Additionally, the TiaRecon™ software may include a list of patients customized for each doctor, a barcode scanner, an image scanner and data extractor (to extract data surrounding a barcode), and encrypted communications including video, audio, and text between devices. The TiaRecon™ software may be integrated with existing billing systems for insurance providers. For example, the software may allow a doctor to enter patient identifying information, such as an SSN or a barcode on a health insurance card, enter information regarding the services provided by the doctor to the patient, and directly submit a bill to the patient's health insurance provider from within the application.

A software component in accordance with an embodiment of the present invention is called Directory or TiaHub™. The Directory component, also referred to as the Directory App, may provide a listing of health care providers, including doctors and other health care employees. Doctors may be listed by specialty, location, affiliations, or insurance plans accepted. The Directory App may allow for encrypted video or voice conferencing and or information exchange, such as textual or image data. Patients may use the Directory App to locate or communicate with a doctor, while doctors may use the Directory App to interact with one another or with their patients.

One or more of the software components may include a universal uploader module, which may access medical information stored on a plurality of formats and transmit that information to the server 102 to be added to a database, which may then be accessed using one or more of the other software components. For example, EMR or DICOM files may be collected using the universal uploader so as to allow a doctor located remotely to quickly and securely access the information.

One or more of the software components may include a diagnosis tracker. The diagnosis tracker allows a doctor to track his patient's symptoms and compare them to those commonly associated with one or more diagnoses. One or more software components may be configured to receive alerts, such as those originating from a patient monitoring system. One or more of the software components may allow a doctor to interact with remotely located medical equipment, sending commands and receiving information from the equipment. One or more of the software components may allow a doctor to access a patient's EMR and/or update a patient's EMR, based on new developments.

In accordance with an embodiment of the present invention, a single electronic health record system (termed NuMR™) is provided for integrating with the various medical equipment and computing devices. An electronic health record is a digital collection of patient information compiled at one or more meetings in any care delivery setting. A patient's record typically includes patient demographics, progress notes, problems, medications, vital signs, past medical history, immunizations, laboratory data, and radiology reports. NuMR™ provides a web browser and/or application-based system available on multiple platforms which provides access to electronic health records. As discussed in greater detail below, NuMR™ enables information to be quickly and seamlessly shared between patients, physicians, billers, pharmacists, treatment facilities, and integrated medical equipment. In an embodiment, NuMR™ enables a physician to electronically prescribe medication to patient based on a remove evaluation performed by the physician. In an embodiment, the software is configured to permit a physician to refer a patient to another physician or consult with another physician for a second opinion, request and review the results of lab tests or imaging tests performed at a remove medical facility, bill a patient for services rendered, schedule appointments or evaluations that may be conducted in person or remotely, access electronic patient medical histories, and securely communicate with a patient using video, audio, and text communications. An example of an exemplary use of the software is discussed below, with reference to FIG. 14. In an embodiment, the software may be secured so as to be compliant with the Health Insurance Portability and Accountability Act ("HIPAA") in protecting personal health information ("PHI").

In an embodiment, an application referred to as TiaRecon™ or TiaCoder™ is provided to help physicians with the process of capturing charges. This application captures the total cost and data from admitting a patient until discharge. Data transmission encrypts and uses standard formats to facilitate ready integration with existing billing software. In an embodiment, a physician simply scans the barcode on an invoice to send the invoice to billers for further processing.

In an embodiment, a secure portal (termed TiaMD™) is provided for enabling remote doctor/patient interaction. TiaMD combines high-quality audio and video conferencing, as discussed above, with the capability to send secure textual or graphical information. Information (e.g., data files generated by medical equipment) may also be exchanged.

In an embodiment, software modules are configured to provide automated alerts and/or automatically schedule and provide a remote consultation between a patient and a physician if the patient's vitals (e.g., blood pressure, weight, or blood oxidation) crosses a predetermined "normal" value.

By way of example and not limitation, for a patient using the BP Unit discussed above, the software may be configured to obtain a measurement of the patient's blood pressure periodically (e.g., once per day or once per hour). This measurement is recorded using a server, as described above. If at any point the patient's measured blood pressure drops below a predefined limit, the server is configured to immediately send an alert to the patient and/or physician (e.g., using a secure text message sent via TiaMD). The software can schedule a remote consultation between the doctor and physician for the next morning, which may be conducted using the software and specialized hardware described herein.

Examples of Use

In order to more fully explain the present invention, the following illustrative examples are provided of circumstances in which embodiments of the present invention may be employed.

Figure 14:
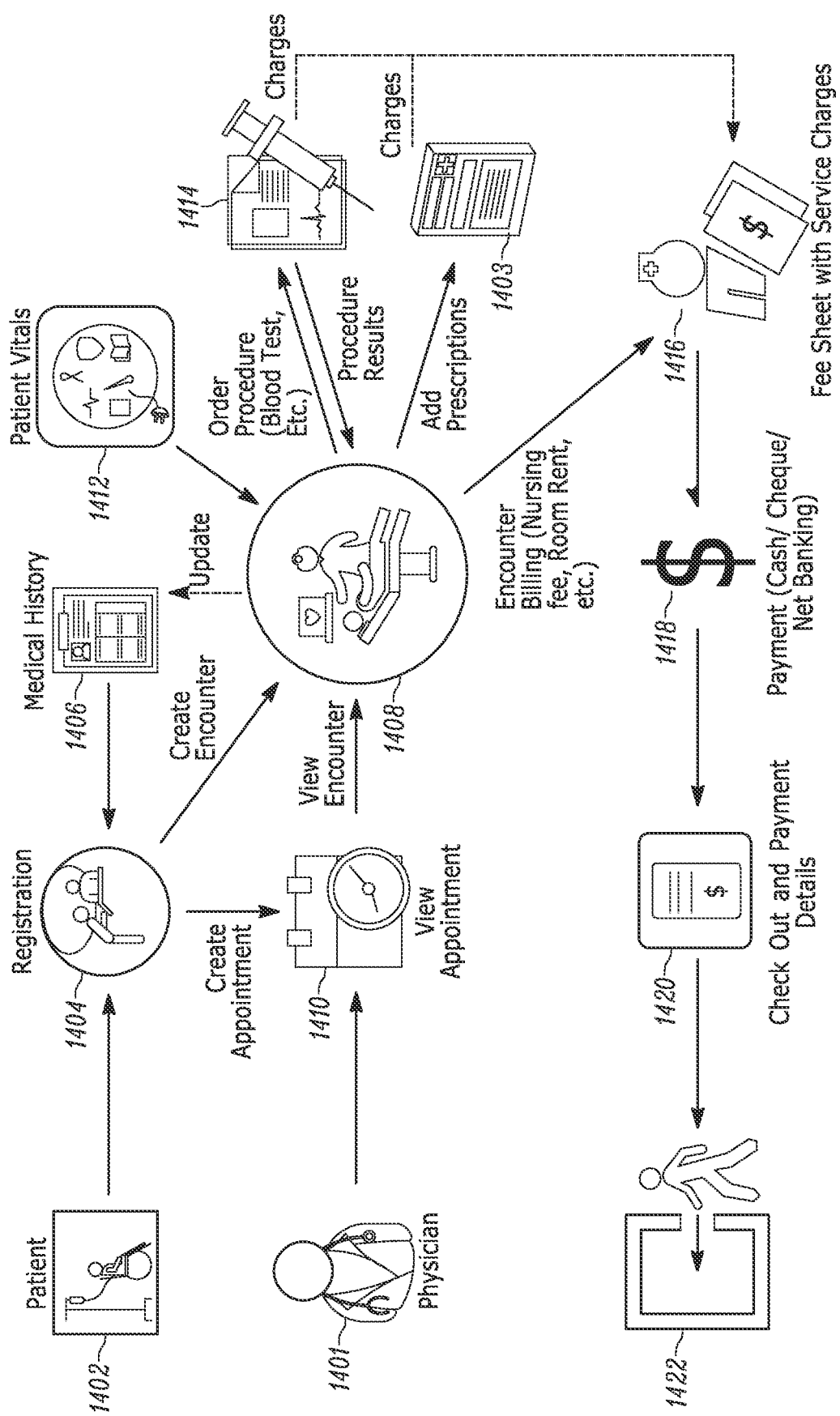
FIG. 14 depicts a block diagram of a method of providing telemedicine in accordance with an embodiment of the present invention.

As shown in FIG. 14, in an exemplary embodiment, a method of providing telemedicine coordinates interactions between a physician 1401, a patient, a pharmacist, and/or a billing department. The method begins when a patient 1402 seeking treatment registers 1404. Based on a preliminary screening and a review of the patient's current medical history 1406, an evaluation (also termed an encounter 1408) is scheduled. If necessary, a physician 1401 is scheduled to be available during the encounter 1408, either in the same physical location or in a different physical location. The appointment is created 1410 and may be viewed using the system by either the patient 1402 or physician 1401. During the encounter 1408, the patient is examined. In an embodiment, the physician interacts with the patient remotely. The physician may request that the patient's vital information be measured 1412 and/or that one or more procedures 1414 (e.g., a blood test) be performed. The results of the encounter are recorded in the patient's medical history 1406, any necessary prescriptions are sent to a pharmacist 1403, and any resulting charges for the encounter 1408 (e.g., room fee, nursing fee, etc.) are compiled into a central database or fee sheet. Similarly, the charges for any procedures 1414 or prescriptions filled by the pharmacist 1403 are compiled on the fee sheet 1416. The patient 1402 provides a single payment 1418 to a payment processor 1420, which is distributed to the physician 1401, pharmacist 1403 and/or a treatment facility as needed. The method ends at step 1422, as the treated patient leaves with access to his or her medical records, any necessary prescriptions, and the ability to easily register for further treatment in the future.

Figure 15:
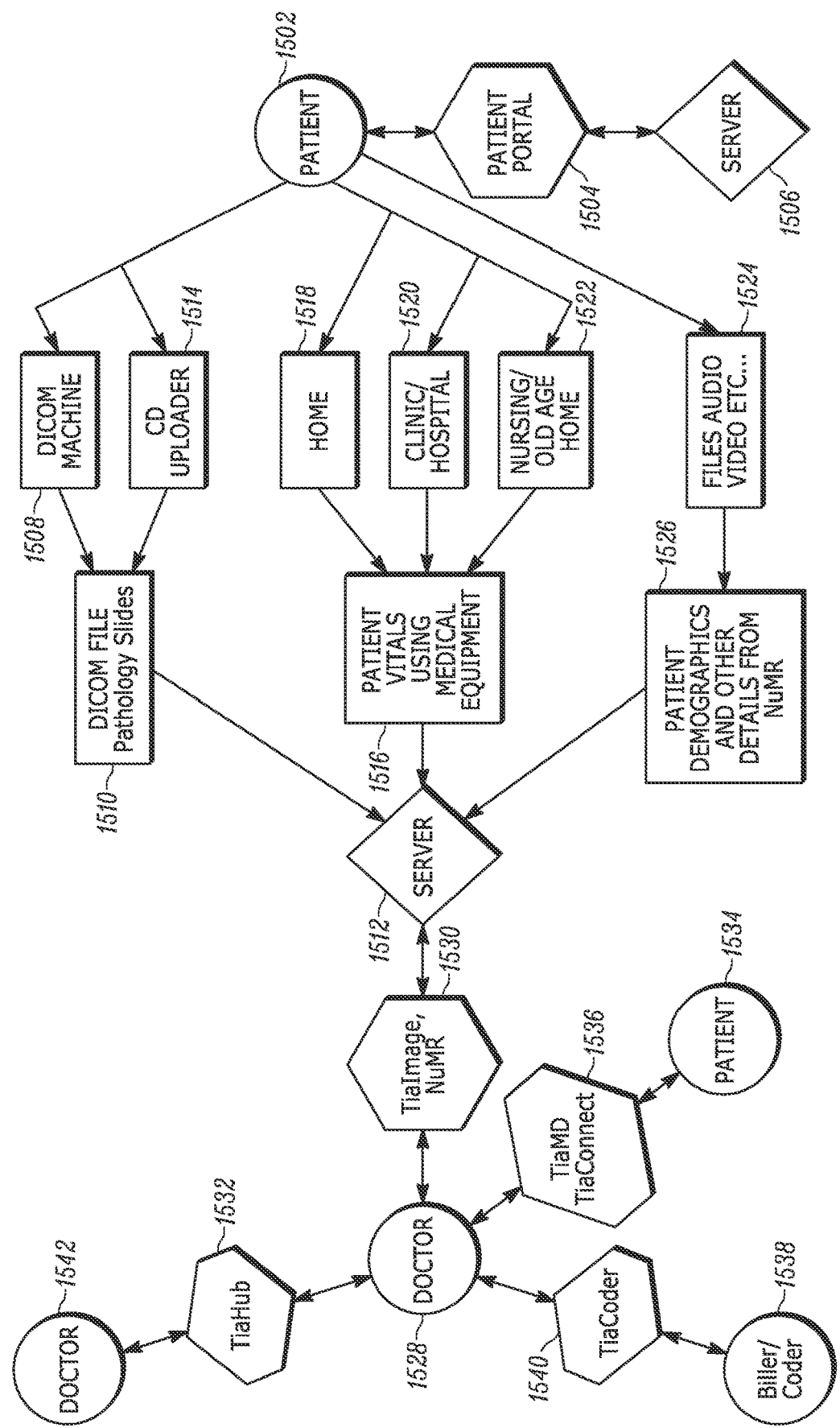
FIG. 15 depicts a block diagram of a method of providing telemedicine in accordance with an embodiment of the present invention.

With reference to FIG. 15, a flow chart depicting the interactions between individuals and the various components of a system in accordance with an embodiment is provided. As shown, a patient 1502 may use the patient portal 1504 to access information previously collected, which is stored on a server 1506 (e.g., the patient's medical records or a directory of physicians able to provide treatment, diagnosis, or assistance to the patient). New information may be collected from the patient in several ways: first, the patient may visit a treatment facility, where medical procedures (e.g., x-ray, EKG) are performed. The results of these tests or procedures are recorded by a DICOM machine 1508 and uploaded to a server 1512 as DICOM files 1510. Alternatively, a patient may use a CD uploader 1514 to upload DICOM files previously generated from past procedures to the server 1512. Second, the patient can use specialized medical equipment 1516 such as that discussed above (e.g., the Height Unit, Weight Unit, BP Unit) to directly upload new information (e.g., patient vital signs or test results) to the server 1512. This equipment 1516 may be located in the patient's home 1518, at a treatment facility 1520 such as a clinic or hospital, or at another location 1522 such as a nursing home. Finally, the patient can directly create files such as video or audio recordings 1524 (for example, using the patient's own personal computer or other computing device) which may be loaded onto the server 1512 using NuMR 1526. A doctor 1528 may then access all of the information stored on the server 1512 using TiaImage or NuMR. That same doctor 1528 may consult with a colleague 1542 using TiaHub 1532, interact with the patient 1534 using TiaMD or TiaConnect, and interact with the biller 1538 using TiaCoder 1540. The servers 1506 and 1512 may be the same server and the patients 1502 and 1534 may be the same patient, thereby allowing a patient to access all of his or her information at any time and interact with his or her physician directly at any point.

As an additional illustrative example, equipment in accordance with an embodiment of the present invention may be carried onboard an aircraft. A base station may be integrated into the aircraft's systems or may be a stand-alone unit. As described above, the base station may contain a communication module capable of accessing a WAN such as the Internet, for example, by using a satellite connection. The base station may further comprise a video camera, microphone, display screen, and speakers. Accordingly, were a medical emergency to occur while the aircraft was in flight, the base station could be used to allow a doctor not present on the aircraft to examine, diagnose, and recommend treatment for the afflicted person.

Similarly, in another example, equipment in accordance with an embodiment of the present invention may be transported to remote areas where trained health care providers are uncommon or unavailable. The equipment may contain multiple communication devices so as to be operable in a variety of circumstances. The equipment may contain a cellular antenna compatible with a variety of SIM cards, a satellite connection, a radio, or other communication devices.

A device in accordance with an embodiment of the present invention includes software for automatically collecting a patient history and performing an initial examination of the patient. The device may include a video camera, microphone, and/or other sensors such as ultrasonic sensors. The device may further include a video screen and speakers. The device may be programmed to display an animation which asks the patient a series of questions, such as "What is your name?" and "How old are you?" The animation may further instruct the patient to perform certain movements, such as raising her arms above her head. The device may record the patient's answers using video, audio, and the data collected by the one or more sensors. After the information is collected and stored, it may be transmitted to a server or other computing device for review by a doctor. In this way, the doctor can quickly receive comprehensive information about a patient without needing to spend time performing the initial examination of the patient. Further, the software may automatically screen for serious conditions that require immediate medical attention, such as traumatic injuries, and prioritize treatment for such patients.

Having thus described in detail preferred embodiments of the present invention, it is to be understood that the invention defined by the above paragraphs is not to be limited to particular details set forth in the above description, as many apparent variations thereof are possible without departing from the spirit or scope of the present invention.

What is claimed is:

1. A system for collecting and relaying medical information, the system comprising:
a base station at a first location, the base station comprising a processor operatively connected to a base station communication module configured to communicate over a local area network using a first communication interface and over a wide area network using a second communication interface, wherein the processor is configured to securely relay commands received over the wide area network to the local area network and relay data received over the local area network to the wide area network;
a medical device proximate the first location comprising a microcontroller operatively connected to a power supply, a device communication module communicatively coupled to the base station via the local area network, and a sensor configured to collect medical information, wherein said microcontroller is configured to transmit the medical information to the base station communication module via the local area network using the device communication module and receive instructions from the base station via the local area network using the device communication module; and
a controller at a second location that is distinct from the first location, the controller comprising a controller communication module communicatively coupled to the base station via the wide area network, wherein the controller is configured to remotely control the medical device by transmitting commands to the base station and is configured to receive the medical information from the base station;
wherein the medical device comprises a stethoscope module, the sensor comprises a plurality of microphones, and the medical information comprises a sound recording, wherein the stethoscope module further comprises:
a body substantially enclosing the microcontroller, the power supply, and the device communication module, the body comprising:
a pair of earpiece connectors separated by a central portion and located at opposite ends of the body, each earpiece connector containing one of the plurality of microphones and configured to receive and support a respective stethoscope earpiece proximate to the respective stethoscope earpiece;
a third microphone attached to the central portion and configured so as to be placed proximate to a patient's chest; and
an input device operatively connected to the microcontroller;
wherein the microcontroller is configured to selectively, based on a signal received from the input device, obtain the sound recording from the first microphone or the second microphone;
wherein the microcontroller is configured to selectively, based on the signal received from the input device, obtain the sound recording from the third microphone; and
wherein the microcontroller is configured to transmit the sound recording to the base station using the device communication module.

2. The system of claim 1, further comprising a storage server at a third location that is distinct from the first and second locations, the storage server comprising a server processor operatively connected to a server communication module that is communicatively coupled to the controller and the base station via the wide area network, and a storage device containing a database, wherein the server is configured to receive medical information from the base station via the wide area network and add the medical information to the database and transmit a portion of the database to the controller.

3. The system of claim 2, wherein said controller further comprises a display and is configured to combine and display the medical information received from the base station and the portion of the database received from the server.

4. The system of claim 2, wherein the server further comprises an alert module configured to monitor medical information received from the base station via the wide area network and notify the base station and controller if a characteristic of the medical information exceeds a predetermined threshold.

5. The system of claim 1, wherein the medical device is a first medical device, the sensor is a first sensor, the device communication module is a first device communication module, the body is a first body, the microcontroller is a first microcontroller, and the power supply is a first power supply;
wherein the medical information includes first medical information from the first medical device;
wherein the system further comprises a second medical device having a second sensor, a second device communication module, a second body, and a second power supply;
wherein the medical information further includes second medical information from the second medical device; and
wherein the second medical device comprises a height unit, the second sensor comprises an accelerometer and an ultrasonic sensor, and the second medical information comprises a height measurement, wherein the height unit further comprises:
a second body comprising an interior surface configured to rest against a person's head and an exterior surface disposed opposite thereto such that the second microcontroller, the second power supply, the second device communication module and the accelerometer are substantially enclosed within the second body; and
an arm containing the ultrasonic sensor in a lower surface thereof, wherein the arm is attached to the second body and projects longitudinally away from the exterior surface such that when the interior surface is in contact with the person's head, the arm extends substantially horizontally and the ultrasonic sensor is oriented substantially vertically;
wherein, the second microcontroller is configured such that upon receiving a signal from the accelerometer indicating that the arm is substantially horizontal, the second microcontroller obtains a distance measurement from the ultrasonic sensor and determines the height measurement based on the distance measurement.

6. The system of claim 1, wherein the medical device is a first medical device, the sensor is a first sensor, the device communication module is a first device communication module, the body is a first body, the microcontroller is a first microcontroller, and the power supply is a first power supply;
wherein the medical information includes first medical information from the first medical device;

wherein the system further comprises a second medical device having a second sensor, a second device communication module, a second body, and a second power supply;

wherein the medical information further includes second medical information from the second medical device; and wherein the second medical device comprises a weight unit, the second sensor comprises a load cell, and the second medical information comprises a weight measurement, wherein the weight unit further comprises:

a second body substantially enclosing the second microcontroller, the second power supply, and the second device communication module, the second body comprising a lower surface spaced apart from and substantially parallel to an upper surface with the load cell located therebetween such that force applied to the upper surface is transferred to the lower surface through the load cell and the accelerometer are substantially enclosed within the second body; and wherein the second microcontroller is configured to, upon receiving a signal from the load cell, determine a weight measurement based on the electrical signal and transmit the weight measurement to the base station using the second device communication module.

7. The system of claim 1, wherein the medical device is a first medical device, the sensor is a first sensor, the device communication module is a first device communication module, the body is a first body, the microcontroller is a first microcontroller, and the power supply is a first power supply;

wherein the medical information includes first medical information from the first medical device;

wherein the system further comprises a second medical device having a second sensor, a second device communication module, a second body, and a second power supply;

wherein the medical information further includes second medical information from the second medical device; and wherein the second medical device comprises a pulse oximeter, the second sensor comprises an infrared LED, a red LED and a photodiode, and the second medical information comprises an oxygen saturation measurement, wherein the pulse oximeter further comprises:

a second body substantially enclosing the second microcontroller, the second power supply, and the second device communication module, the second body comprising:

an interior surface configured to be placed adjacent to and in contact with a finger and an exterior surface opposing the interior surface;

a lower portion containing the infrared LED and the red LED located on the interior surface thereof; and an upper portion spaced apart from the lower portion and containing the photodiode located on the interior surface thereof such that the photodiode is located opposite the infrared LED and the red LED;

wherein the second microcontroller is configured to selectively activate and deactivate the infrared LED and the red LED, obtain a plurality of measurements from the photodiode, calculate the oxygen saturation measurement based on the plurality of measurements, and transmit the oxygen saturation measurement to the base station using the second device communication module.

8. The system of claim 1, wherein the medical device is a first medical device, the sensor is a first sensor, the device communication module is a first device communication module, the body is a first body, the microcontroller is a first microcontroller, and the power supply is a first power supply;

wherein the medical information includes first medical information from the first medical device;

wherein the system further comprises a second medical device having a second sensor, a second device communication module, a second body, and a second power supply;

wherein the medical information further includes second medical information from the second medical device; and wherein the second medical device comprises a blood pressure measurement unit, the second sensor comprises a pressure gauge and a transducer, and the second medical information comprises a blood pressure measurement, wherein the blood pressure measurement unit further comprises:

a second body substantially enclosing the second microcontroller, the second power supply, and the second device communication module in a central portion thereof, the second body comprising:

a display operatively connected to the second microcontroller;

an input device operatively connected to the second microcontroller;

a cuff configured to encircle an arm, wherein the transducer is mounted in the cuff and is configured to measure vibrations in arteries located in the arm; and an automatic pump operatively connected to the second microcontroller and configured to inflate the cuff;

wherein the pressure gauge is configured to measure the pressure in the cuff;

wherein the second microcontroller is configured to:
activate the pump upon receiving an initiation signal from the input device,
deactivate the pump upon determining that the pressure in the cuff has reached a first threshold
obtain a first pressure reading upon determining based on the signal provided by the transducer that blood has begun to flow intermittently,
obtain a second pressure reading upon determining based on the signal provided by the transducer that blood has begun to continuously flow,
determine the blood pressure measurement based on the first and second pressure readings, and
transmit the blood pressure measurement to the base station using the second device communication module.

9. The system of claim 2, wherein the medical device is a first medical device, the system further comprising:

a second medical device selected from the group consisting of a height unit, a weight unit, a pulse oximeter, and a blood pressure measurement unit, wherein the first medical device is different from the second medical device;

wherein the server is configured to receive first medical information via the base station from the first medical device and second medical information via the base station from the second medical device and add both the first and second medical information to the database.

10. The system of claim 1, wherein the base station further comprises an automation unit configured to receive a plurality of first automation instructions from the controller via the wide area network and transmit a plurality of second automation instructions via the local area network, the system further comprising:
- a TV module containing a TV microcontroller operatively connected to a TV communication unit and an infrared emitter, wherein the TV module is operatively connected to a television via the infrared emitter, the TV communication unit is communicatively coupled to the base station and the TV microcontroller is configured to operate the television based on a first one or more of the plurality of second automation instructions received from the base station; and
- a lighting module containing a lighting microcontroller and operatively connected to a lighting communication unit, wherein the lighting module is operatively connected to a light source, the lighting communication unit is communicatively coupled to the base station and the lighting microcontroller is configured to control the light source based on a second one or more of the plurality of second automation instructions received from the base station.

11. The system of claim 1, wherein the base station further comprises an alarm unit, the system further comprising:
- a motion detector located in the first location, the motion detector comprising a motion microprocessor operatively coupled to a motion sensor and a motion communication unit, wherein the motion communication unit is communicatively coupled to the base station and the motion microcontroller is configured to determine whether there is motion in the first location and, upon determining motion is present in the first location, transmit a motion signal to the base station;

wherein the alarm unit is configured to analyze the medical information and the motion signal and determine whether to issue an alert based on a plurality of predefined rules;

wherein, upon determining to issue the alert, the alarm unit is configured to transmit the alert to the controller.

12. A method of using the system of claim 1, comprising the steps of:
- registering a patient with a central server and uploading the patient's medical history to the central server;
- scheduling an appointment between the patient and a physician based on information obtained during the patient's registration and based on the patient's medical history;
- performing an evaluation, wherein the patient is located in a first location and the physician is located in a second location that is different than the first location, wherein the evaluation comprises gathering medical information regarding the patient using one or more medical devices which are controlled by and relay the medical information to the physician;
- updating the patient's medical history on the central server with the medical information obtained during the evaluation;
- scheduling a procedure at a medical facility based on the results of the evaluation;
- providing the results of the procedure to the physician and updating the patient's medical history on the central server;
- providing the patient with a prescription to be filled by a pharmacist at the medical facility;
- collecting all charges incurred by the patient in the evaluation and procedure for the prescription onto a single fee sheet;
- collecting a single payment from the patient for the amount on the fee sheet; and
- distributing the single payment proportionally to the physician and the medical facility.

* * * * *